(12) United States Patent
Mietzner et al.

(10) Patent No.: US 10,808,216 B2
(45) Date of Patent: Oct. 20, 2020

(54) REACTOR SURFACE FINISH REMEDIATION

(71) Applicant: Lonza Ltd., Visp (CH)

(72) Inventors: Michael Mietzner, Freemont, NH (US); Jim Heimbach, Springvale, ME (US); Andrew Harris, Allendale, NJ (US)

(73) Assignee: Lonza Ltd, Visp (CH)

( * ) Notice: Subject to any disclaimer, the term of this patent is extended or adjusted under 35 U.S.C. 154(b) by 549 days.

(21) Appl. No.: 15/285,656

(22) Filed: Oct. 5, 2016

(65) Prior Publication Data

US 2018/0094231 A1  Apr. 5, 2018

(51) Int. Cl.
*G01D 21/02* (2006.01)
*C12M 1/12* (2006.01)

(52) U.S. Cl.
CPC .................................. *C12M 37/06* (2013.01)

(58) Field of Classification Search
CPC ..................................... G01B 21/30; G01B 1/00
See application file for complete search history.

(56) References Cited

U.S. PATENT DOCUMENTS

| | | | | |
|---|---|---|---|---|
| 3,729,812 A | * | 5/1973 | Thomas | B21D 51/20 228/155 |
| 5,165,246 A | * | 11/1992 | Cipolla | F17C 9/00 137/210 |
| 5,392,797 A | * | 2/1995 | Welch | B08B 9/0323 134/108 |
| 5,656,491 A | | 8/1997 | Cassani et al. | |
| 5,705,082 A | * | 1/1998 | Hinson | C23F 1/02 216/100 |
| 5,762,641 A | * | 6/1998 | Bewick-Sonntag | A61F 13/15203 604/378 |
| 6,103,361 A | * | 8/2000 | Batzar | B05D 3/207 427/127 |
| 7,629,167 B2 | | 12/2009 | Hodge et al. | |
| 8,298,054 B2 | | 10/2012 | Hodge et al. | |
| 8,771,635 B2 | | 7/2014 | Mohtadi et al. | |
| 9,388,373 B2 | | 7/2016 | Rao et al. | |
| 2003/0189053 A1 | * | 10/2003 | Felbaum | F17C 1/02 220/582 |
| 2009/0305626 A1 | | 12/2009 | Hope | |
| 2012/0077429 A1 | | 3/2012 | Wernimont et al. | |
| 2015/0353371 A1 | * | 12/2015 | Caton | B01F 5/0405 423/376 |

\* cited by examiner

*Primary Examiner* — Lisa M Caputo
*Assistant Examiner* — Alex T Devito
(74) *Attorney, Agent, or Firm* — Dority & Manning, P.A.

(57) ABSTRACT

Improved biopharmaceutical processing equipment such as reactor vessels and stainless steel surfaces, and methods of determining the same are disclosed herein. In some embodiments, a biopharmaceutical processing equipment can include a vessel having a surface that is configured to contact proteinaceous processing material, wherein the surface has a pre-commissioning surface roughness of greater than about 20 Ra Max (μin).

17 Claims, 20 Drawing Sheets

Pitting

Scratching

Roughness

Micro pitting

| | | Depth - mm | | | | |
|---|---|---|---|---|---|---|
| | | 0.2 | 1.2 | 2.6 | 4 | 5 |
| Diameter (mm) | 1.2 | | 0% | | 0% | |
| | 2.6 | 0% | | 0% | | 0% |
| | 4 | | 0% | | 50% | |
| | 5 | 0% | | 100% | | 66% |

FIG. 8

R²: 22.31%
p-values
Density Factor: 0.911
Pit Depth: 0.930
Aspect Ratio: 0.960
Density Factor*Pit Depth: 0.561
Pit Depth*Aspect Ratio: 0.950
Cleaning Agent : 0.006

REACTOR SURFACE FINISH REMEDIATION

BACKGROUND

The present disclosure relates to bioreactor vessels and production surfaces, and more specifically, to cleanability of bioreactor vessels and production surfaces.

In the pharmaceutical and biopharmaceutical industries, stainless steel equipment surface finishes are carefully controlled to ensure a high degree of cleaning capability. Prior to commissioning, this is accomplished by developing robust design specifications and confirming compliance during qualification. Once commissioned, equipment must be inspected using an on-going maintenance program to identify when surfaces require restoration. In both pre- and post-commissioning, however, suitable levels of surface anomalies and their impact on cleanability was previously unknown causing increased remediation among vessels already commissioned and added expense in the commissioning, construction, and operational maintenance of vessels due to inconsistent and uncontrolled surface characteristic requirements.

As such, improved reactor vessels and stainless steel surfaces and methods of determining the same are desired.

SUMMARY

Improved biopharmaceutical processing equipment such as reactor vessels and stainless steel surfaces, and methods of determining the same are disclosed herein. In some embodiments, a biopharmaceutical processing equipment can include a vessel having a surface that is configured to contact proteinaceous processing material, wherein the surface has a pre-commissioning surface roughness of greater than about 20 Ra Max (μin). In some embodiments, the surface can have a pre-commissioning surface roughness of greater than about 35 Ra Max (μin). In some embodiments, the surface can have a pre-commissioning surface roughness of greater than about 20 Ra Max (μin) and less than or equal to about 250 Ra Max (μin). In some embodiments, the surface can have a pre-commissioning surface roughness of greater than about 35 Ra Max (μin) and less than or equal to about 150 Ra Max (μin). In some embodiments, the surface can have a pre-commissioning surface roughness of greater than about 90 Ra Max (μin) and less than or equal to about 150 Ra Max (μin). In some embodiments, the surface can have a pre-commissioning surface roughness of about 150 Ra Max (μin). In some embodiments, the surface can be formed of 316L stainless steel.

In at least one embodiment, a biopharmaceutical processing equipment, can include a vessel having a surface that is configured to contact proteinaceous processing material, wherein the surface has a surface finish that is free of a surface anomaly that exceeds a maximum depth of surface pitting of about 2.6 mm. Moreover, in some embodiments, the processing equipment surface can be free of a surface anomaly that exceeds a maximum scratch depth of about 1.0 mm. In some embodiments, the surface can be free of a surface anomaly that exceeds a maximum depth of surface pitting of about 1.2 mm. The surface can be formed of 316L stainless steel. In some embodiments, the surface can have a pre-commissioning surface roughness of greater than about 20 Ra Max (μin). In some embodiments, the surface can have a pre-commissioning surface roughness of greater than about 35 Ra Max (μin). In some embodiments, the surface can have a pre-commissioning surface roughness of greater than about 20 Ra and less than or equal to about 250 Ra Max (μin). In some embodiments, the surface can have a pre-commissioning surface roughness of greater than about 35 Ra and less than or equal to about 250 Ra Max (μin). In some embodiments, the surface can have a pre-commissioning surface roughness of greater than about 35 Ra and less than or equal to about 150 Ra Max (μin). In some embodiments, the surface can have a pre-commissioning surface roughness of about 150 Ra Max (μin). In some embodiments, the surface can have a surface finish that is free of a surface anomaly that exceeds any of: a maximum depth of surface pitting of about 1.2 mm, and a maximum scratch depth of about 1.0 mm.

In some embodiments, a method of repairing biopharmaceutical processing equipment can include inspecting a surface of a vessel that is in contact with processing materials for the presence of a surface anomaly, determining a physical characteristic of the surface anomaly on the surface, and remediating the surface anomaly from the surface if the surface anomaly exceeds a predetermined threshold. In some embodiments, the physical characteristic can be a pit depth and/or a scratch depth. In some embodiments, the surface anomaly can be a pit and the predetermined threshold is a maximum pit depth of about 2.6 mm. In some embodiments, the surface anomaly can be a pit and the predetermined threshold can be a maximum pit depth of about 1.2 mm. In some embodiments, the surface anomaly can be a micropit and the predetermined threshold can be a maximum micropit density of about 2600 per inspection area. In some embodiments, the surface anomaly can be a scratch and the predetermined threshold can be a maximum scratch depth of about 1.0 mm. In some embodiments, the surface anomaly can be surface roughness and the predetermined threshold can be a surface finish of up to about 150 Ra Max (μin). In some embodiments, the predetermined threshold can include a maximum pit depth of about 1.2 mm, a maximum micropit density of about 2600 per inspection area, a maximum scratch depth of about 1.0 mm, and/or a surface finish of up to about 150 Ra Max (μin). In some embodiments, inspecting a surface of the vessel that is in contact with processing materials for the presence of surface anomaly can include at least one of visually inspecting the surface of the reactor vessel and using a depth gauge instrument for measuring a depth of an anomaly. Remediating the surface anomaly from the surface can include buffing the surface with a buffing apparatus sufficient to remove the surface anomaly.

BRIEF DESCRIPTION OF THE DRAWINGS

FIG. 8 illustrates visual effects of fluorescence using UV lighting captured as a percent of coupons failing visual inspections within a two-variable matrix consisting of depth and diameter;

DETAILED DESCRIPTION

Figure 1:
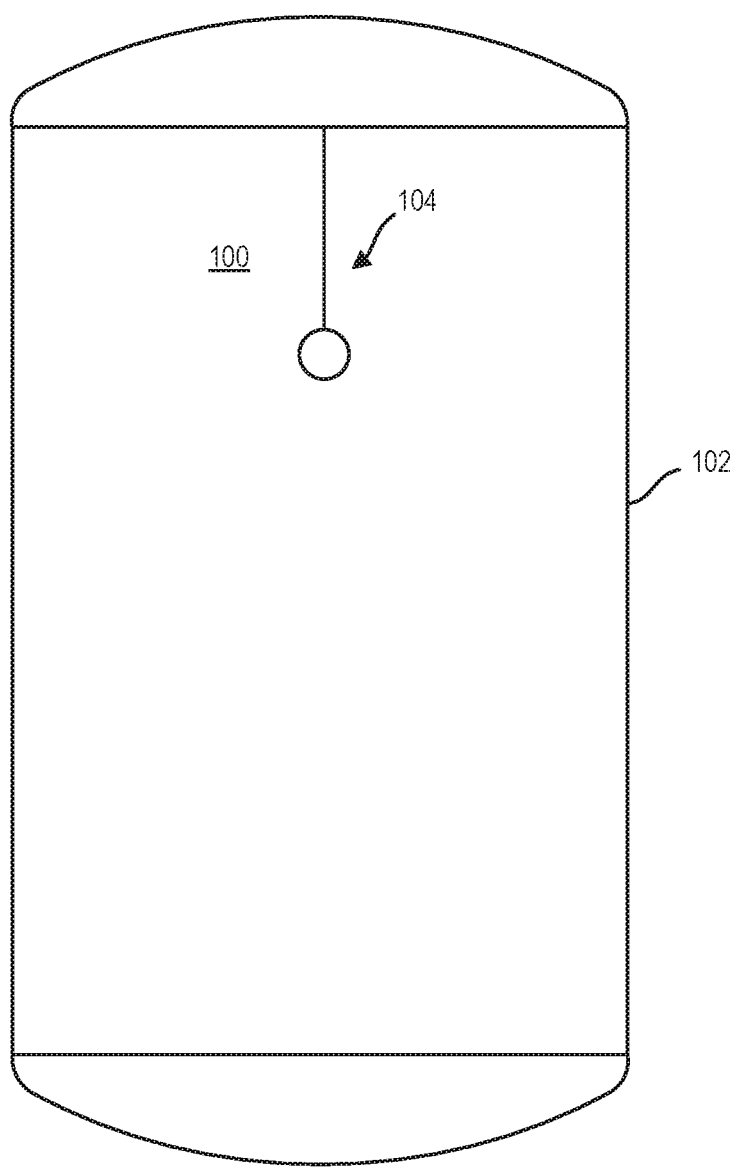
FIG. 1 illustrates an example biopharmaceutical reactor vessel.

As stated above, the present disclosure relates to bioreactor vessels and production surfaces, and more specifically, to cleanability of bioreactor vessels and production surfaces, which are now described in detail with accompanying figures. It is noted that like reference numerals refer to like elements across different embodiments.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

The biopharmaceutical and pharmaceutical industries have largely adopted stringent specifications based on the 2014 edition of the American Society of Mechanical Engineers' Bioprocessing Equipment (ASME BPE) standards that define the acceptable level surface anomalies on vessel surfaces—such as pitting, scratching, and surface finish deviations—that can be tolerated for routine operations within a given system. As used herein, "surface anomaly" means any imperfection on a given surface, whether formed pre- or post-commissioning. For example, four types of surface imperfections are commonly observed in biopharmaceutical manufacturing product contact surfaces—scratches, roughness, micropits, and pitting. As used herein "pre-commissioning" means during the design and production of the reactor before the reactor is placed into service and used in the production of a product. As used herein "post-commissioning" means after the reactor has been placed into service to produce a product. As used herein, "pit" or "pitting" is a surface void having a measurable depth that is generally annular, circular, oval, or oblong in shape. As used herein, "scratch" means a surface void having a substantially linear shape with a measurable depth. As used herein, "vessel," "reactor vessel," and/or "processing equipment" means any device or system with at least one surface that comes in contact with process materials, including but not limited to tanks, pipes, filters, bioreactors, product hold vessels, WFI hold vessels, chromatography skids, ultrafiltration/diafiltration skids, filter housings, and any process contact surface that is cleaned via recirculating CIP.

Table SF-2.4-1 of the ASME BPE (2014), which is hereby incorporated by reference in its entirety and reproduced in part below, establishes guidelines for the biopharmaceutical industry regarding surface roughness (as shown in $R_a$ Max in both microinches and microns) for commissioned reactors. Adopting these standards has led to challenges in on-going maintenance as tanks age. Features such as pit diameter are extremely difficult to measure in the field once equipment is in operation. And, while other industry publications have explored the impact of surface finish on biofilm formation, prior to this disclosure nothing indicated imperfections exceeding these ASME BPE specifications are detrimental to chemical cleaning (such as CIP) performance.

TABLE SF-2.4-1

$R_a$ Readings for Metallic Process Contact Surfaces

| Surface Designation | $R_a$ Max. | |
|---|---|---|
| | µin. | µm |
| Mechanically Polished [Note (1)] | | |
| SF0 | No finish requirement | No finish requirement |
| SF1 | 20 | 0.51 |
| SF2 | 25 | 0.64 |
| SF3 | 30 | 0.76 |
| Mechanically Polished [Note (1)] and Electropolished | | |
| SF4 | 15 | 0.38 |
| SF5 | 20 | 0.51 |
| SF6 | 25 | 0.64 |

GENERAL NOTES:
(a) All $R_a$ readings are to be in accordance with ASME B46.1.
(b) All $R_a$ readings are taken across the lay, wherever possible.
(c) No single $R_a$ reading shall exceed the $R_a$ max. value in this table.
(d) Other $R_a$ readings are available if agreed upon between owner/user and supplier, not to exceed values in this table.
NOTE:
(1) Or any other finishing method that meets $R_a$ max.

As used below, surface roughness is measured as $R_a$ Max in microinches (μin) (hereinafter referred to as "Ra Max (μin)").

As will be described in detail herein, adoption of these standards may be overly stringent or smooth and thus have added expense to manufacturing as cost of reactor materials increases with decreased surface roughness; i.e., the smoother the surface, the more expensive the material. As such, an aspect of this disclosure is to provide a qualitative and quantitative threshold determination for pre- and post-commission analysis of biopharmaceutical reactor vessels as well as methods of analyzing, cleaning, and designing, building, and/or repairing reactors based on application of these thresholds.

As described herein, an objective of this disclosure is to better define criteria for remediation by evaluating when cleaning capability is affected by aging and/or chemical degradation of product contact surfaces. As is described below, the impact of pits, scratches, and surface finish changes was explored in a laboratory setting using a broad cross section of soil types and cleaning conditions to identify true inflection points in cleaning degradation. These studies explored a wide range outside the typical boundaries of imperfections in order to provide sound statistical basis for conclusions. As such, this disclosure identifies thresholds or inflection points that can be used as the basis to define surface anomaly action limits as part of a visual inspection and/or maintenance program or during the commission of new reactor vessels.

As described herein, the cleaning effect of surface anomalies or imperfections was explored using a difficult to remove proteinaceous soil of bovine serum albumin (BSA) applied to the surface through immersion in an agitated solution. As used herein, "proteinaceous" means any substance, such as a fluid, containing at least one protein, amino acid residue, or other organic molecule typically associated with biopharmaceutical production including but not limited to lipids and other macro molecules. This particular proteinacious soil served as a surrogate to challenge the cleaning capability with precisely controlled surface imperfections.

Taking into consideration all of the data and observations described in the Examples, the following thresholds can be applied (together or separately) to determine the cleanability of a reactor surface and/or the need for remediating a surface anomaly, and may serve as the basis of a visual inspection program:
1. Pitting is not impactful to cleanability as long as pit depths are maintained at less than about 2.6 mm and, in some embodiments, equal to or less than about 1.2 mm. At these depths, pit density and diameter are irrelevant.
2. Scratches are not impactful to cleanability as long as scratch depths are maintained at less than about 1.2 mm and, in some embodiments, equal to or less than about 1.0 mm. Scratch length and angle were irrelevant within the ranges shown herein.
3. Micropits are not impactful to cleanability up to at least about 2600 per inspection area.
4. Surface finish is not impactful to cleanability up to at least about 150 Ra Max (μin).

These thresholds can be applied to the commission of a reactor vessel and/or the remediation or repair of a reactor vessel surface. That is, these thresholds can be applied when designing and building a reactor vessel as well as during maintenance of on-line reactors. Any suitable remediation method can be utilized. For example, a buffing apparatus—such as a grinder—can be used to remove the surface anomaly from the surface. In embodiments, for example, remediation can include backweld filling the anomaly and then grind smooth.

FIG. 1 illustrates an example biopharmaceutical reactor vessel. As shown, in FIG. 1, a reactor vessel 100 can have a reactor surface 102 that is configured to contact proteinaceous processing material—such as a fermentation media and inoculant—and a CIP apparatus 104 configured to clean the reactor surface 102. The reactor vessel 100 can include any other components necessary for production of biopharmaceuticals such as sensors, probes, baffles, inlets, outlets, and any other component (not shown). In some aspects, the reactor vessel 100 and reactor surface 102 is formed from stainless steel such as 316L, 304, or other 18-8 stainless steels. Other metals, such as Inconel, titanium alloys, and others may be used as is suitable to a particular application and production method.

In some embodiments, the reactor surface 102 can have a surface finish that is free of surface anomalies that exceed the thresholds described herein. For example, the reactor surface 102 can be free of pits that are equal to or exceed a maximum depth of surface pitting of about 2.6 mm. In some embodiments, the surface 102 can be free of pits that are equal to or exceed a maximum depth of about 1.2 mm. In some embodiments, the surface 102 can be free of scratches that are equal to or exceed a maximum scratch depth of about 1.2 mm. In some embodiments, the surface 102 can be free of scratches that are equal to or exceed a maximum scratch depth of about 1.0 mm. As such, the cleanability of the reactor surface using standard CIP cleaning techniques is assured.

Also, in some embodiments, the reactor surface 102 can have a surface finish that is greater than about 20 Ra Max (μin). For example, the reactor surface 102 can have a surface finish of between about 20 Ra Max (μin) and about 250 Ra Max (μin), and preferably about 150 Ra Max (μin). In some embodiments, the surface 102 can have a surface finish that is greater than about 35 Ra Max (μin). In some embodiments the surface 102 can have a surface finish of between about 35 Ra Max (μin) and about 250 Ra Max (μin), and preferably about 150 Ra Max (μin). Also, in some embodiments, the reactor surface 102 can be free of micropit density of more than about 2600 per inspection area.

As described, the reactor vessels can be commissioned to include a less-smooth surface pre-commissioning, i.e., the reactor can be designed and built using a rougher steel than has previously been practiced in industry. That is, reactors and reactor surfaces that are in contact with process fluids can have a surface roughness of greater than 20 Ra Max (μin), such as between about 20 Ra Max (μin) and about 150 Ra Max (μin). That is not to say that a surface roughness of 20 Ra Max (μin) and below is inconsistent with the teachings of this disclosure—acceptable cleaning of reactor surfaces with roughness of 20 Ra Max (μin) and below is achieved—but surface roughness above 20 Ra Max (μin) may be employed and as a result the initial cost to build reactors and future remediation costs are decreased relative to a surface roughness of 20 Ra Max (μin) and below. For example, in some embodiments prior to bringing brought on-line or pre-commissioning, a reactor surface 102 can have a surface roughness of about 25 Ra Max (μin), about 30 Ra Max (μin), about 40 Ra Max (μin), about 50 Ra Max (μin), about 60 Ra Max (μin), about 70 Ra Max (μin), about 80 Ra Max (μin), about 90 Ra Max (μin), about 100 Ra Max (μin), about 110 Ra Max (μin), about 120 Ra Max (μin), about 130 Ra Max (μin), about 140 Ra Max (μin), about 150 Ra Max (μin), about 160 Ra Max (μin), about 170 Ra Max (μin), about 180

Ra Max (μin), about 190 Ra Max (μin), and about 200 Ra Max (μin). In some embodiments, surfaces can have a pre-commissioning surface roughness of greater than about 35 Ra Max (μin). Preferably, in some embodiments, reactor surfaces have a pre-commissioning surface roughness of between about 60 Ra Max (μin) and about 150 Ra Max (μin). Preferably, in some embodiments, reactor surfaces have a pre-commissioning surface roughness of about 150 Ra Max (μin).

These thresholds can be applied to any bioreactor vessel and/or production surface such as those that require CIP cleaning, and particularly those that are configured to contain proteinaceous materials such as reactors for cultivating cells.

EXAMPLES

Various Examples are included to illustrate the determination of appropriate surface anomaly thresholds for biopharmaceutical manufacturing surfaces. The Examples studied the effect on cleanability of several factors affecting tank finish that have been observed in stainless steel processing equipment. This disclosure identifies inflection points that can be used as the basis to define surface anomaly action limits as part of a visual inspection and/or maintenance program or in the commission of new reactor vessels.

Example Methods

Coupons were manufactured with pits, scratches, and roughness characteristics designed to bracket the current AMSE BPE guidance for new tanks and extend to points of inflection. As will be described in more detail below, for scratches, roughness, and micropitting; a single-variable study was executed. Scratches were assessed at varying depths encompassing ASME BPE ranges that had been created diagonally across a coupon. Each coupon had only one scratch. Surface roughness was assessed from 20 Ra Max (μin) to 150 Ra Max (μin). Micropits, with depths that could not be quantified, were generated using electrochemical etching. This allowed an assessment of micropit density using the specification of 40 pits per inspection area and an exaggerated condition of 2600 pits per inspection area. Pitting defects were the largest group of the study and included exploration of aspect ratio (defined as depth of the pit divided by the diameter) and density. A half-fraction designed experimental approach was used to determine the influence and interaction (if any) of these surface imperfections on cleaning ability.

Surface finish studies in these experiments were executed using coupons made of ¼" thick stainless steel 316L (SS316L) plate with a base finish of 20 Ra Max (μin) except where noted to represent typical pressure vessel construction materials. The coupons were manufactured using multiple vendors to achieve the desired imperfections. Pitted coupons were milled by drilling at desired depths and diameters.

Surface roughness, as measured by Ra Max (μin), was designed as a single factor experiment. Coupons of 30 Ra Max (μin), 60 Ra Max (μin), 90 Ra Max (μin), 120 Ra Max (μin), and 150 Ra Max (μin) were generated for this assessment for comparison with the baseline 20 Ra Max (μin) coupons. The element of scratch depth was also explored as a single factor. These were generated using a metal cutting disc with the same length (50.8 mm), at a 45° angle across the coupon, and a minimized width of 1.0 mm. Only the depth was varied. Nine coupons were generated with scratch depths of 0.2 mm, 0.4 mm, 0.6 mm, 0.8 mm, 1.0 mm, 1.2 mm, 2.6 mm, 4.0 mm, and 5.0 mm.

For the studies with the pits and scratches, it was decided to execute the studies with the milled imperfections without exposure to additional corrosion. This was done to avoid adding additional uncontrolled variability to the studies. To investigate the impact of corrosive effects, micropitted coupons were electrochemically generated. A grid with evenly distributed holes punched into contact paper was placed over the coupon. The paper was used to mask areas subjected to electrochemical etching while the holes allowed current to flow at the localized points. The etching took place in an acid/salt bath using a stainless steel probe connected to an electrical current. The anode was applied to the coupon and the cathode to the probe. One coupon was generated with 40 micro-pits and another coupon was generated with 2600 micro-pits.

Two full-factorial designed experiments for pitting were utilized. These designs provided the template for a half factorial approach resulting in five (5) different density components, five (5) different pit depths, and five (5) different diameters. The combination of depth and diameter also gave rise to a fourth implicit variable of aspect ratio (depth/diameter). For analysis, aspect ratio; depth; and density were evaluated. The choice of variables was based on field experience and the difficult in diameter measurement of pits in actual equipment.

Figure 2:
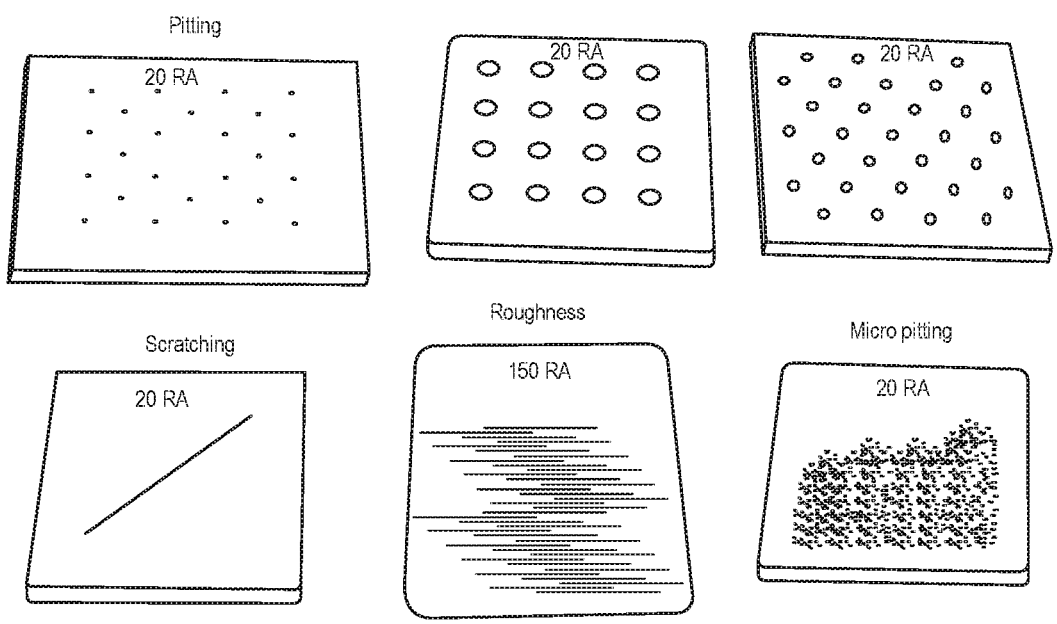
FIG. 2 illustrates pitted, scratched, roughened, and micropitted coupons.

Only one coupon of each type was generated. Replicates were achieved by preparing and cleaning each coupon at least three (3) times over the course of multiple days. The specific set of pitted coupons reported in this paper is detailed below in Table 4. Additionally, FIG. 2 illustrates pitted, scratched, roughened, and micro-pitted coupons showing the various types of factors explored.

TABLE 4

Coupon Factors - Density, Diameter, Depth, and Aspect Ratio

| Coupon | Density Factor | Diameter (mm) | Depth (mm) | Aspect Ratio (depth/diameter) |
|---|---|---|---|---|
| P-03 | 1.0 | 2.6 | 2.6 | 1.00 |
| P-04 | 1.0 | 5.0 | 0.2 | 0.04 |
| P-05 | 1.0 | 5.0 | 5.0 | 1.00 |
| P-06 | 1.8 | 1.2 | 1.2 | 1.00 |
| P-07 | 1.8 | 1.2 | 4.0 | 3.33 |
| P-08 | 1.8 | 4.0 | 1.2 | 0.30 |
| P-09 | 1.8 | 4.0 | 4.0 | 1.00 |
| P-11 | 3.0 | 2.6 | 0.2 | 0.09 |
| P-12 | 3.0 | 2.6 | 2.6 | 1.00 |
| P-13 | 3.0 | 2.6 | 5.0 | 1.91 |
| P-14 | 3.0 | 5.0 | 2.6 | 0.52 |
| P-15 | 4.2 | 1.2 | 1.2 | 1.00 |
| P-16 | 4.2 | 1.2 | 4.0 | 3.33 |
| P-17 | 4.2 | 4.0 | 1.2 | 0.30 |
| P-18 | 4.2 | 4.0 | 4.0 | 1.00 |
| P-21 | 5.0 | 2.6 | 2.6 | 1.00 |
| P-22 | 5.0 | 5.0 | 0.2 | 0.04 |
| P-23 | 5.0 | 5.0 | 5.0 | 1.00 |

Residue Soiling of Coupons:

Prior to application of the residue to the coupons in this design, all coupons were cleaned using a method similar to USP <1051> Cleaning Glass Apparatus. Table 5 summarizes the cleaning process. Cleaning with the CIP-100 chemical was carried out in an ultrasonic bath. CIP 100® Alkaline Process and Research Cleaner is commercially available from Steris Corporation.

TABLE 5

Cleaning of Coupons Prior to Testing

| Step | Cleaning Solution | Conc. (% v/v) | Temp. (° C.) | Minimum Cleaning Time (min.) |
|---|---|---|---|---|
| 1 | Manually clean to remove visible residue | | | |
| 2 | CIP-100 | 1.0% | 35° C. | 30 min. |
| 3 | PW | N/A | ~20° C. | 1 rinse per side |
| 4 | $H_3PO_4$ | 0.5% | ~20° C. | 2 min. |
| 5 | PW | N/A | ~20° C. | 6 rinses per side |
| 6 | Perform water break testing per ASTM F22-13 to ensure absence of detectable residue prior to soiling | | | |

Figure 3:
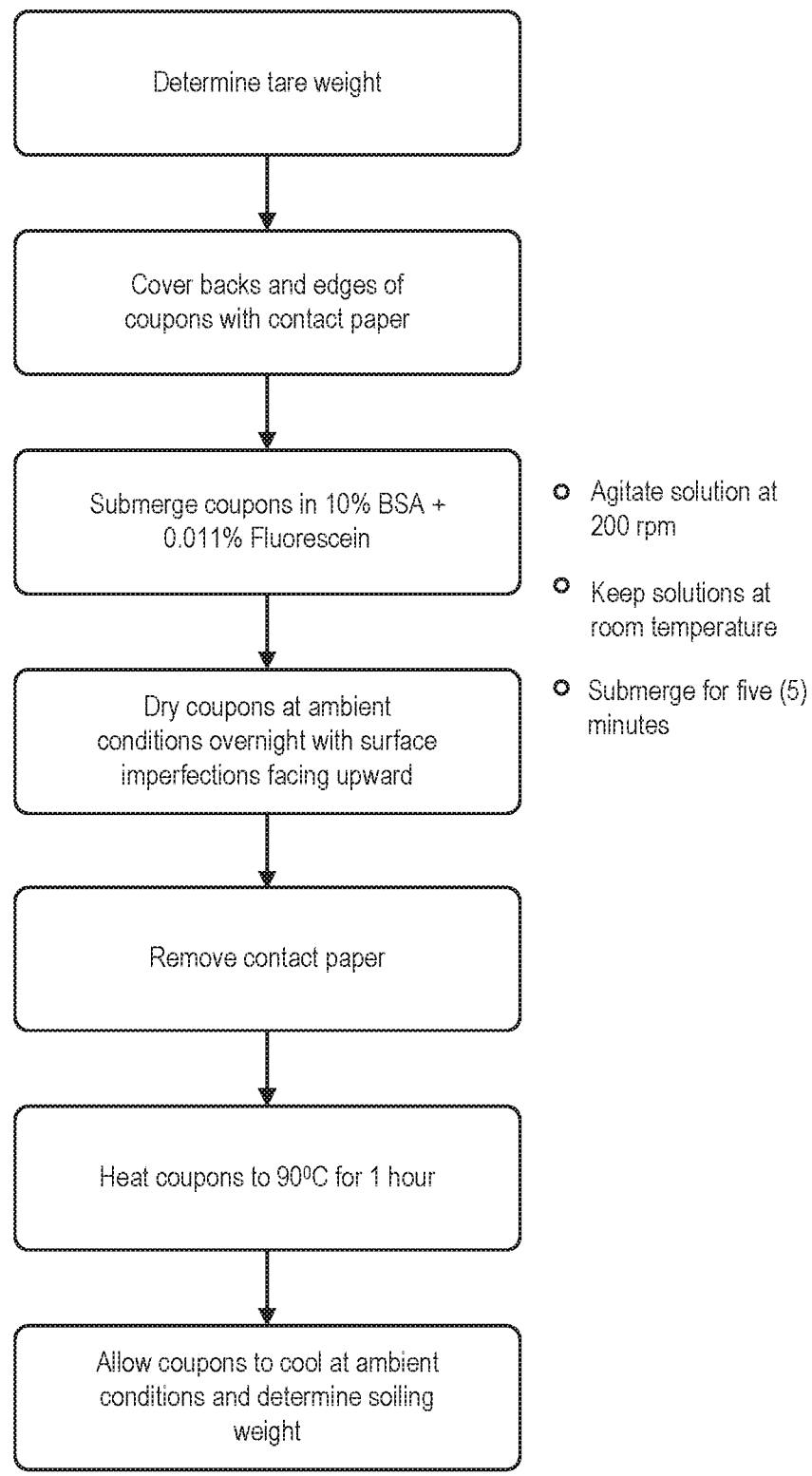
FIG. 3 illustrates an example method for the application of BSA soils onto the pitted, scratched, and roughened coupons.
Figure 4:
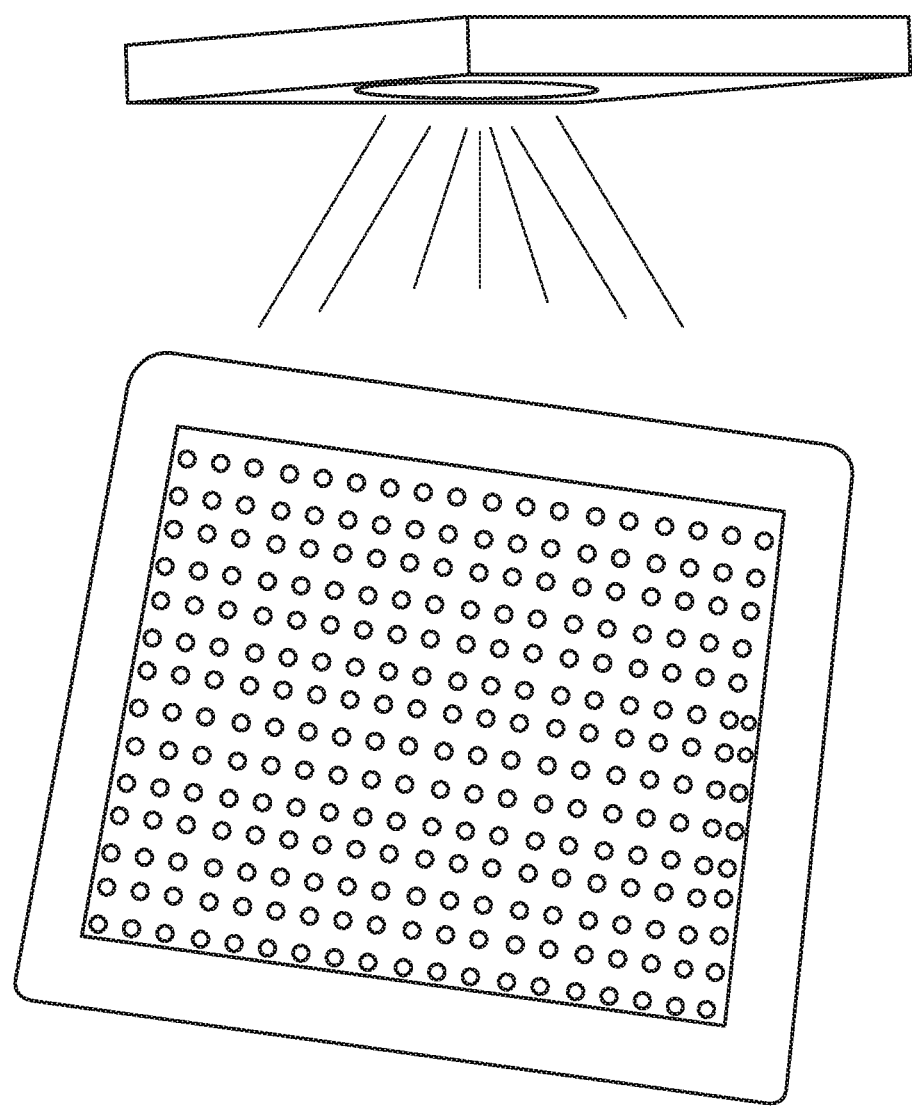
FIG. 4 illustrates an example coupon examined with UV light.

Bovine serum albumin (BSA) was chosen as a protein surrogate to test surface finish cleanability because it is a representative proteinaceous soil whose removal can be tuned through heat treatment to a beta-sheet confirmation. This allowed the removal rates to be carefully controlled to evaluate the relative impact of the surface finish differences. FIG. 3 illustrates an example method for the application of BSA soils onto the pitted, scratched, and roughened coupons. The concentration of BSA and Fluorescein in the mixture was optimized for suitable soiling weights and fluorescent detection. The heat treatment of the coupons after drying caused denaturation of the protein, which enhanced its binding to the coupon's surface. The temperature for heat treatment was empirically determined to optimize the concurrent dissolution of the BSA and Fluorescein. This was accomplished by applying the residues to control coupons and heating the coupons over a range of temperatures from 80 C to 110 C for 60 minutes. The treated coupons were then tested to determine how long it took to remove the Fluorescein (gauged by examination with a UV light under the flow of the cleaning agent, as shown in FIG. 4 illustrating an example coupon examined with UV light) and the BSA (gauged through visual inspection of the coupons under ambient lighting). The test temperature was chosen based on the condition that minimized the time difference between removal of the two component soils while providing a long enough test time to detect differences in conditions. This turned out to be 90° C. heat treatment of the coupons for 60 minutes with a five minute cleaning time to completely remove the BSA soil.

Cleaning of Soiled Coupons

Soiled coupons were cleaned in a caustic commercial cleaning solution for five (5) minutes. This time was empirically determined in screening tests to completely remove the surrogate BSA/Fluorescein mixture from a pristine coupon. The order of coupon exposure to the cleaning regimen described below was randomized for each of the three (3) replicate runs. The orientation of the coupons with respect to the cleaning agent flow was also randomized.

Figure 5:
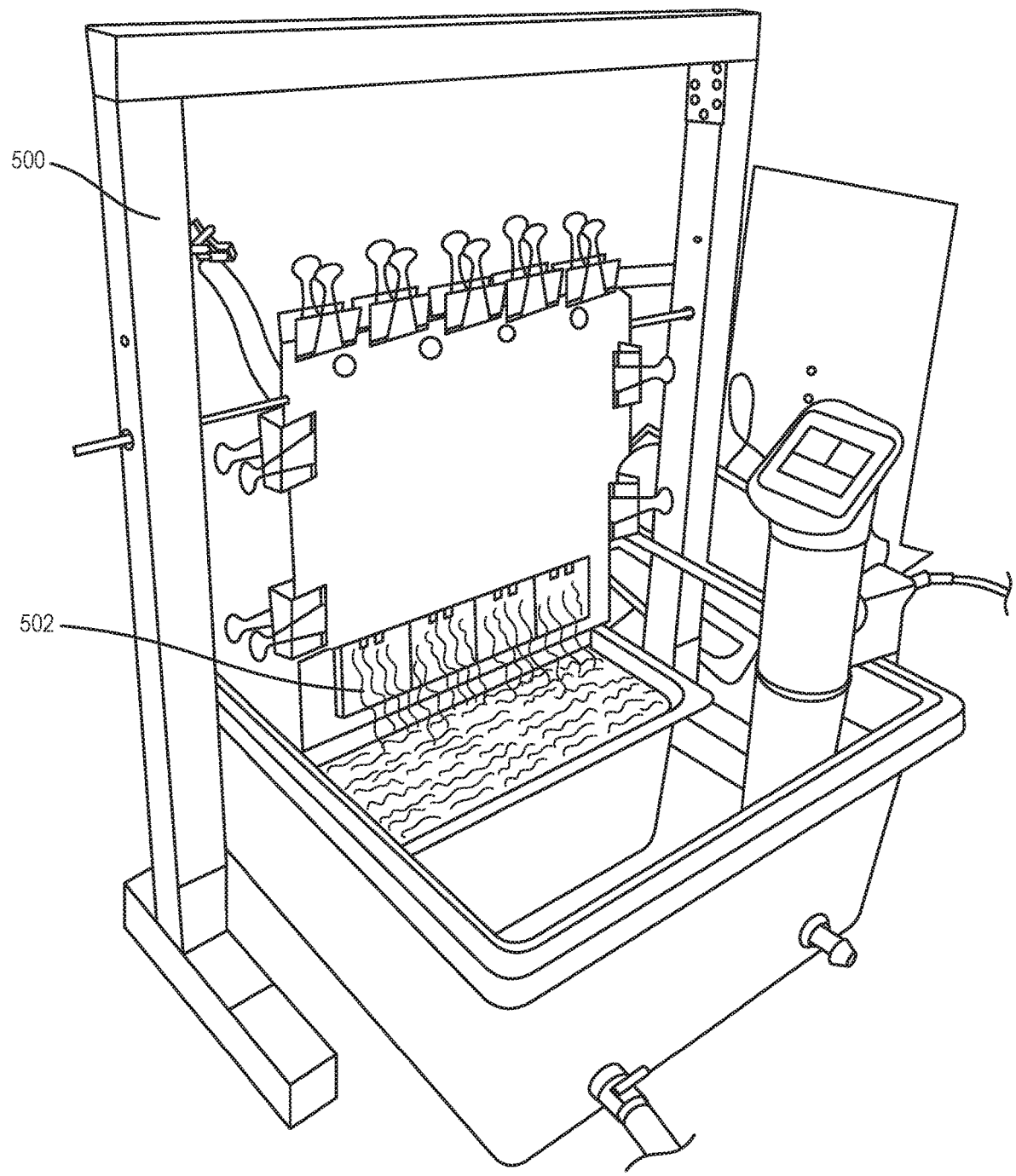
FIG. 5 illustrates an example falling film test apparatus.

FIG. 5 illustrates an example falling film test apparatus 500 utilized in the following examples. As shown, tests were conducted on a falling film system 500 designed to generate energy of flow at 3000 Reynolds number over the coupons 502 for cleaning. The Reynolds number was chosen to simulate the worst case condition of a falling film down the sidewall of the vessel. The cleaning agent solution used was 1% CIP100® (commercially available from Steris) at 60° C. Each set of experiments used two pristine, 20 Ra Max (μin) control coupons to allow relative comparison to coupons with no designed surface imperfections. After cleaning, all coupons 502 were allowed to dry before being assessed for remaining residue.

Evaluating Cleanliness

Three methods were used to evaluate cleanliness: (1) Gravimetric determination was utilized as the primary quantitative approach to assess the removal percentage of the soil; (2) BSA was combined with a Fluorescein marker during some of the studies to allow a qualitative assessment of material retention in the pits as gauged by fluorescence under an ultraviolet light (UV); and (3) worst-case process soils were evaluated with different cleaning cycle recipes to show the applicability of the surface finish results obtained with BSA under simulated process conditions.

In the Addendum Examples, the Total Organic Carbon was also evaluated. The fluorescence method described in point (2), was intended solely for use at the lab scale to enhance visual inspection, provided orthogonal confirmation of cleaning inflection points. These addendum studies using process soils included assessment of residual mass and residual Total Organic Carbon (TOC) using a swab methodology. The TOC testing was included to provide a link to existing cleaning validation test methods.

Gravimetric analysis was used as a quantitative measure of total soil removed, expressed as percent (%) removed. Weights were obtained prior to soiling, after BSA/Fluorescein was applied and heat-treated, and after the cleaning and post drying regimen. Each value was normalized to the controls. For scratches, roughness, and micro-pitting; the normalized controls were also included as part of the continuum of variables. The addition of Fluorescein created a highly sensitive marker, which allowed for evaluation of remaining residue within the pits and other deformities when inspected under UV light. These qualitative and quantitative measures allowed assessment of multiple facets of the surface imperfections on cleaning.

Addendum Examples

The intent of the Addendum Examples was to assess whether the significant variables that hinder cleanability of the protein surrogate could be applied to the worst-case process soils and actual cleaning process parameters. These examples involved two additional residues and five cleaning regimens as demonstrated in Table 6.

The cleaning conditions were selected to represent other typical regimens within a biopharmaceutical facility. The Addendum Examples were designed to bridge the detailed analysis performed using the BSA surrogate soil and CIP 100® with other process soil and cleaning agent combinations. The Addendum Examples assess how other cleaning chemistries paired with their respective process soils could impact the inflection points generated during the primary portion of the study.

TABLE 6

Cleaning Conditions and Soil for Addendum Examples

| Cleaning Conditions | Soil |
|---|---|
| 1% CIP 100 60° C. | Lysate[+] |
| 0.2N NaOH 20° C. | Lysate[+] |
| 1.3% CIP 150 60° C. | Lysate[+] |
| Purified water 80° C. | Lysate[+] |
| 5% CIP100 + 5% CIP Additive 80° C. | Tank ring surrogate* |

[+]Pre-harvest lysate provided as a worst-case soil
*Tank ring surrogate = 1% weight/volume erucamide in ethanol, autoclaved for 48 hours A subset of the initial coupons was chosen from the DOE consisting of pitted coupons, scratched coupons, and pristine coupon controls. These coupons are listed in Table 7.

TABLE 7

Addendum Coupons

| Coupon | Density Factor | Diameter mm | Pit Depth mm | Aspect Ratio depth/width |
|---|---|---|---|---|
| Control | N/A | N/A | N/A | N/A |
| S-01 | 1 | N/A | 0.2 | N/A |
| S-04 | 1 | | 5.00 | |
| P-04 | 1 | 5 | 0.20 | 0.04 |
| P-23 | 5 | 5 | 5 | 1 |
| P-22 | 5 | 5 | 0.20 | 0.04 |
| P-05 | 1 | 5 | 5.00 | 1.00 |
| P-16 | 4.2 | 1.2 | 4.00 | 3.33 |

Soils were applied as before by dipping the masked coupons in a beaker of the soil. All other procedures outlined under cleaning of the soiled coupons were utilized in assessment in these addendum studies with the exception of cleaning times. The cleaning time for the lysate was determined by the duration to completely clean in 1% CIP 100® at 60° C. using the control coupon. Likewise, for the tank ring surrogate, the time for complete clean of a pristine control coupon was determined under the conditions listed. In addition to gravimetric analysis and inspection with UV fluorescence, Total Organic Carbon (TOC) swab samples with 500 parts per billion as the pass/fail criteria.

Example 1: Pitting

Statistical analysis of the pit data with the BSA surrogate revealed no significant correlations between aspect ratio, depth, and density (p-value >0.05). However, both pit depth (p-value=0.091) and the interaction between pit depth and aspect ratio (p-value=0.064) were near the threshold for statistical significance. This indicates that the depth to diameter interaction may be important for residue removal.

Results of the quantitative and qualitative analysis are summarized in Table 8 below. In these cases, the percent removal is normalized so that the controls represent 100% removal and all other results are reference to these values. The value in parentheses next to the PASS/FAIL indicator for fluorescence represents the percentage of coupons that failed the inspection under UV light.

TABLE 8

Normalized Results for Pitted Coupons

| Coupon | % Removed | Fluorescence |
|---|---|---|
| Control | 100.0 ± 2.8% | Pass |
| P-03 | 94.1 ± 4.2% | Pass |
| P-04 | 97.8 ± 2.8% | Pass |
| P-05 | 94.1 ± 2.1% | Fail (33%) |
| P-06 | 97.2 ± 2.8% | Pass |
| P-07 | 98.9 ± 4.0% | Pass |
| P-08 | 94.7 ± 4.1% | Pass |
| P-09 | 93.8 ± 1.7% | Fail (33%) |
| P-11 | 98.2 ± 5.0% | Pass |
| P-12 | 90.6 ± 1.1% | Pass |
| P-13 | 92.7 ± 4.5% | Pass |
| P-14 | 96.5 ± 4.8% | Fail (100%) |
| P-15 | 92.2 ± 1.7% | Pass |
| P-16 | 95.3 ± 2.6% | Pass |
| P-17 | 96.4 ± 0.8% | Pass |
| P-18 | 90.3 ± 5.1% | Fail (66%) |
| P-21 | 95.7 ± 4.7% | Pass |
| P-22 | 98.0 ± 1.6% | Pass |
| P-23 | 89.2 ± 1.3% | Fail (66%) |

Figure 6:
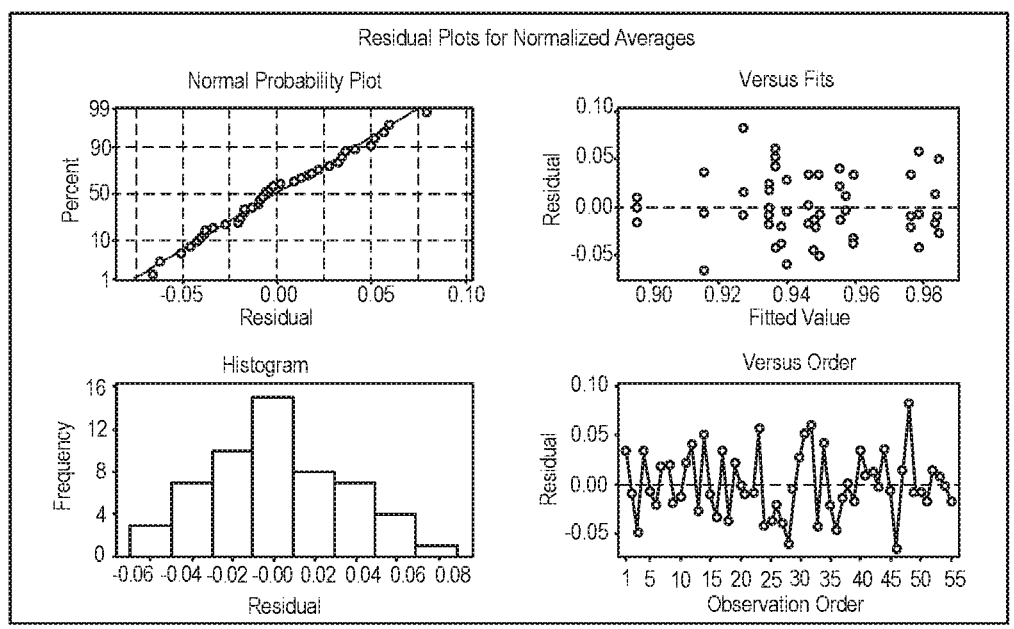
FIG. 6 summarizes regression analysis illustrating multiple regression for % removal as a function of density factor, aspect ratio, and depth.

To evaluate the impact of the different pit variables on removal efficiency, multiple regression was used to test the hypothesis that cleanability is a function of aspect ratio, pit depth, and/or density. Aspect ratio, a function of depth over diameter, is the preferred measurement for pit criteria and was therefore used in the statistical analysis for these data. The combination of all four variables is not appropriate since diameter, pit depth, and aspect ratio are not independent from one another. Only two of these three variables can be analyzed at the same time within the context of this experiment, so depth and aspect ratio were chosen for the evaluation. FIG. 6 summarizes the regression analysis illustrating multiple regression for % removal as a function of density factor, aspect ratio, and depth.

Figure 7:
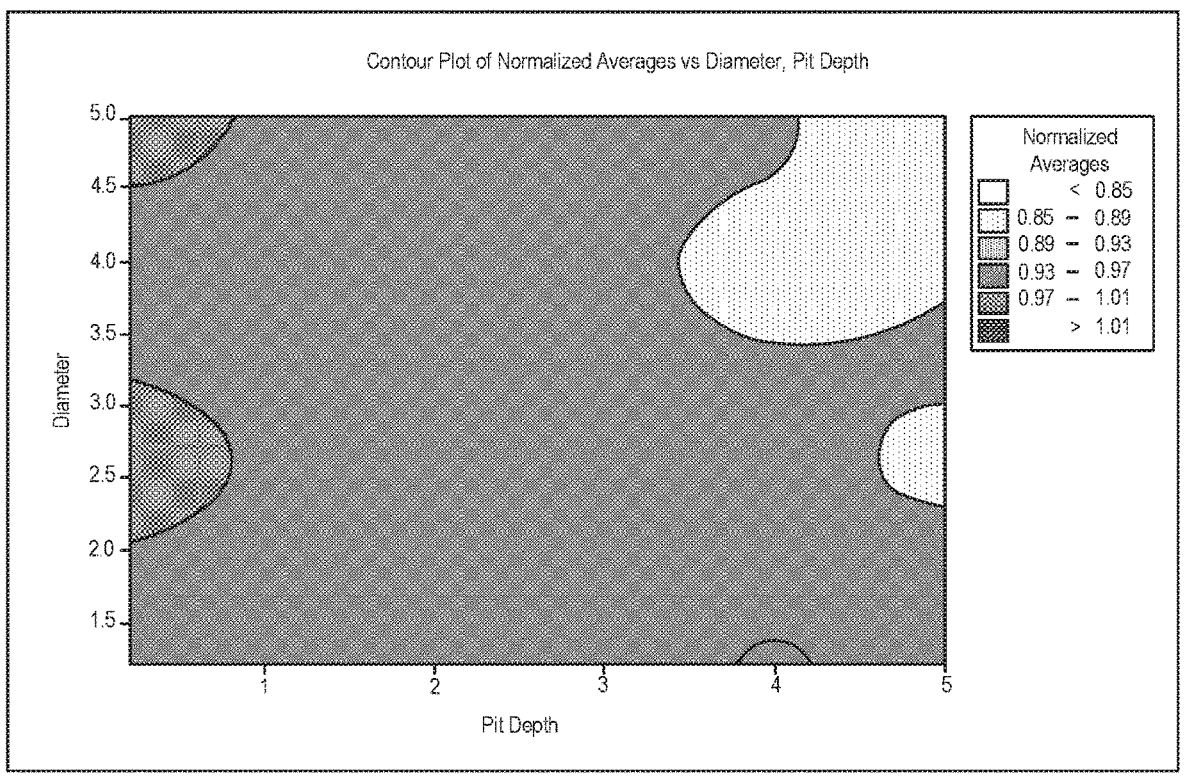
FIG. 7 illustrates contour plots of % removal for pairs of factors.

FIG. 7 illustrates contour plots of % removal for pairs of factors. The contour plots assist in highlighting the area most impacted by pitting. These plots provide preliminary indications of inflection points in residue removal efficiency as a function of the significant variables. The light green areas in the graphs indicate areas with decreased removal efficiency. These would indicate that the quadrant with diameter ≥2.5 mm and depth ≥3.5 mm as most likely to negatively impact cleaning efficiency.

FIG. 8 illustrates visual effects of fluorescence using UV lighting captured as a percent of coupons failing visual inspections within a two-variable matrix consisting of depth and diameter. Using the matrix approach, the graphical depiction of failures shown in FIG. 8 with identified inflection points within the chosen design spaces. The coupons were assigned a pass/fail value. Coupons were considered to fail if any fluorescent residue was detected, regardless of the number of total pits on the surface. Visual inspection using the fluorescent marker detected failures when diameter was ≥4.0 mm combined with a depth ≥2.6 mm. This result is consistent with the regression model showing a propensity for lower mass removal with higher depth and diameter combinations. The results in FIG. 8 help to more conclusively identify the inflection points impacting cleaning capability. The data support the results from the gravimetric analysis by demonstrating the interactive effect of depth and diameter. The conclusions are more discrete than those drawn from the gravimetric analysis, but point to the same general trends. Namely, the quadrant with diameter ≥4.0 mm and depth ≥2.6 mm shows the greatest likelihood to negatively impact cleaning efficiency.

Example 2: Surface Roughness

Figure 9:
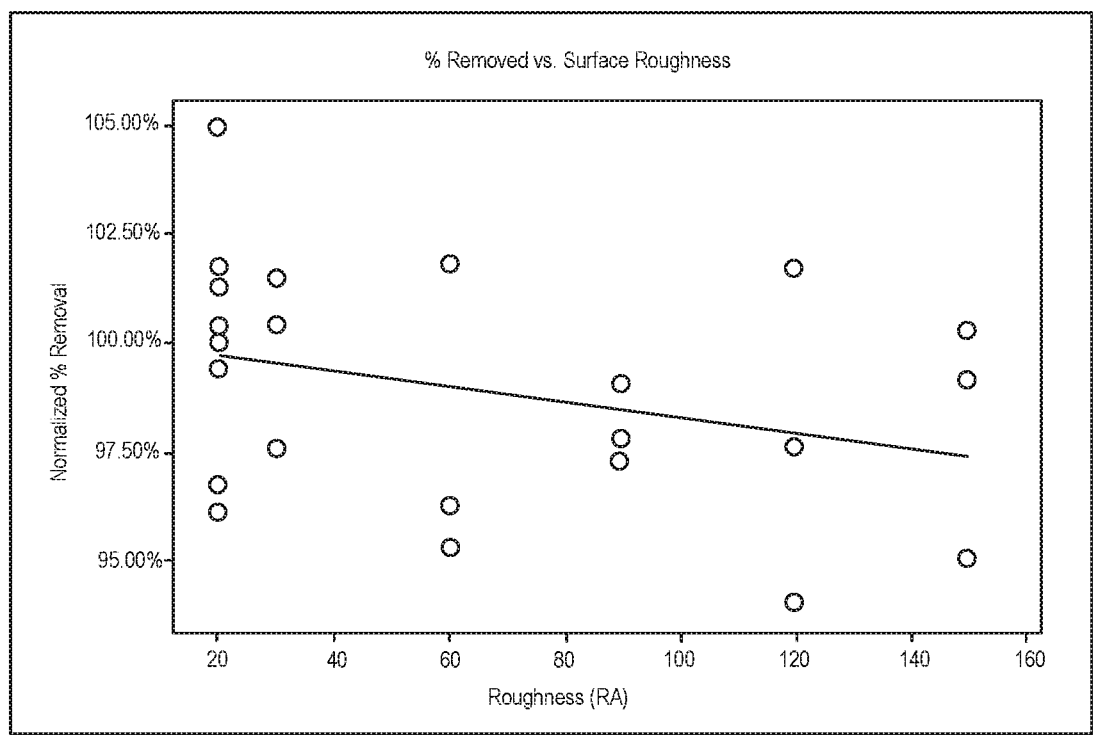
FIG. 9 illustrates a linear regression analyzing "Normalized % Removal" and surface roughness.

Example coupons exploring the effect of surface roughness indicate that surface roughness of between about 20 Ra Max (μin) and about 150 Ra Max (μin) have comparable cleaning efficiency. FIG. 9 illustrates a linear regression used to show that "Normalized % Removal" is a function of surface roughness. The p-value is sufficiently large (p>0.05), thus concluding that percent removal is not a function of surface roughness, at least within the limits tested here. Additionally, there were no visual failures under UV conditions.

The summary data in Table 9 shows comparable cleanability (i.e. >97% mass removal) as the roughness is increased from 20 Ra Max (μin) to 150 Ra Max (μin). This supports the conclusion from the regression analysis.

TABLE 9

Summary of Normalized % Removal by Coupon Roughness

| Coupon | % Removed |
|---|---|
| 150 Ra Max (µin) | 98.1 ± 2.8% |
| 120 Ra Max (µin) | 97.8 ± 3.8% |
| 90 Ra Max (µin) | 98.1 ± 0.9% |
| 60 Ra Max (µin) | 97.8 ± 3.5% |
| 30 Ra Max (µin) | 99.8 ± 2.0% |
| 20 Ra Max (µin) (control) | 100.0 ± 2.8% |

As such, statistical analysis of the surface roughness data revealed no statistical correlation between Ra Max (µin) value and residual mass (p-value >0.05). In addition, no fluorescent failures were noted during visual inspection.

Example 3: Micropits

Statistical analysis of the micropitting data revealed no statistical correlation between density factor and residual mass (p-value >0.05), at least within the ranges tested in Example 3. In addition, no fluorescent failures were noted during visual inspection.

Figure 10:
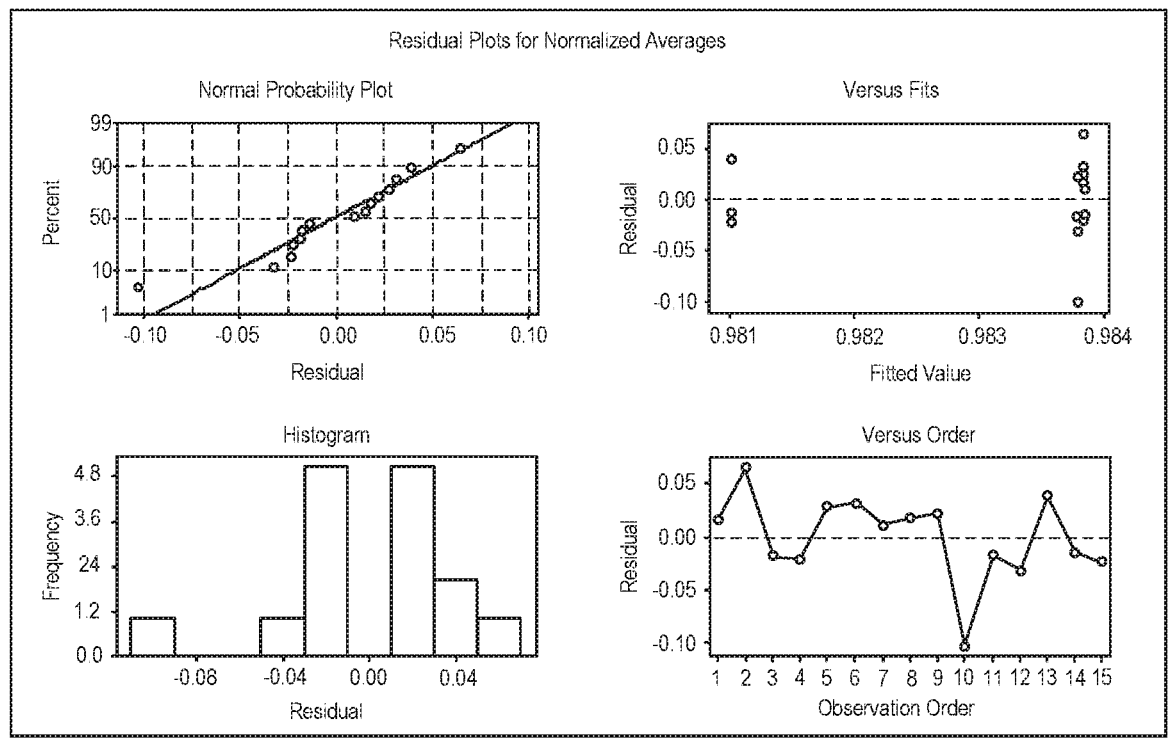
FIG. 10 illustrates residual plots analyzing "Normalized % Removal" and pit density.

FIG. 10 illustrates linear regression methods used to test that "Normalized % Removal" is a function of pit density. As shown in FIG. 10, there was no significant (p>0.05) effect of pit density on percent removal, at least within the range tested in Example 3. There were no visual failures under UV.

A summary of normalized percent removal for the micro-pitted coupons is captured in Table 10.

TABLE 10

Summary of Normalized % Removal for Micropitting

| Density Factor | % Removed |
|---|---|
| 0 (Control) | 100.0 ± 2.8% |
| 40 | 95.1 ± 5.2% |
| 2600 | 98.2 ± 3.3% |

Example 4: Scratch

Statistical analysis of the scratch data with the BSA surrogate revealed a strong correlation between scratch depth and removal efficiency (p-value=0.000) with removal being degraded as scratch depth was increased. Visual inspection using the fluorescent marker detected failures when depth was >1.0 mm.

Results for both cleanliness measures for the scratched coupons are summarized below in Table 11.

TABLE 11

Normalized Results for Scratches

| Scratch Depth | % Removed | Fluorescence |
|---|---|---|
| 0.0 mm | 100.0 ± 2.9% | N/A |
| 0.2 mm | 97.5 ± 3.9% | Pass |
| 0.4 mm | 99.5 ± 0.5% | Pass |
| 0.6 mm | 100.6 ± 7.0% | Pass |
| 0.8 mm | 98.4 ± 2.9% | Pass |
| 1.0 mm | 97.6 ± 4.4% | Pass |
| 1.2 mm | 98.4 ± 4.3% | Fail (17%) |
| 2.6 mm | 96.6 ± 6.2% | Fail (71%) |
| 4.0 mm | 94.2 ± 3.4% | Fail (100%) |
| 5.0 mm | 91.7 ± 4.8% | Fail (86%) |

Figure 11:
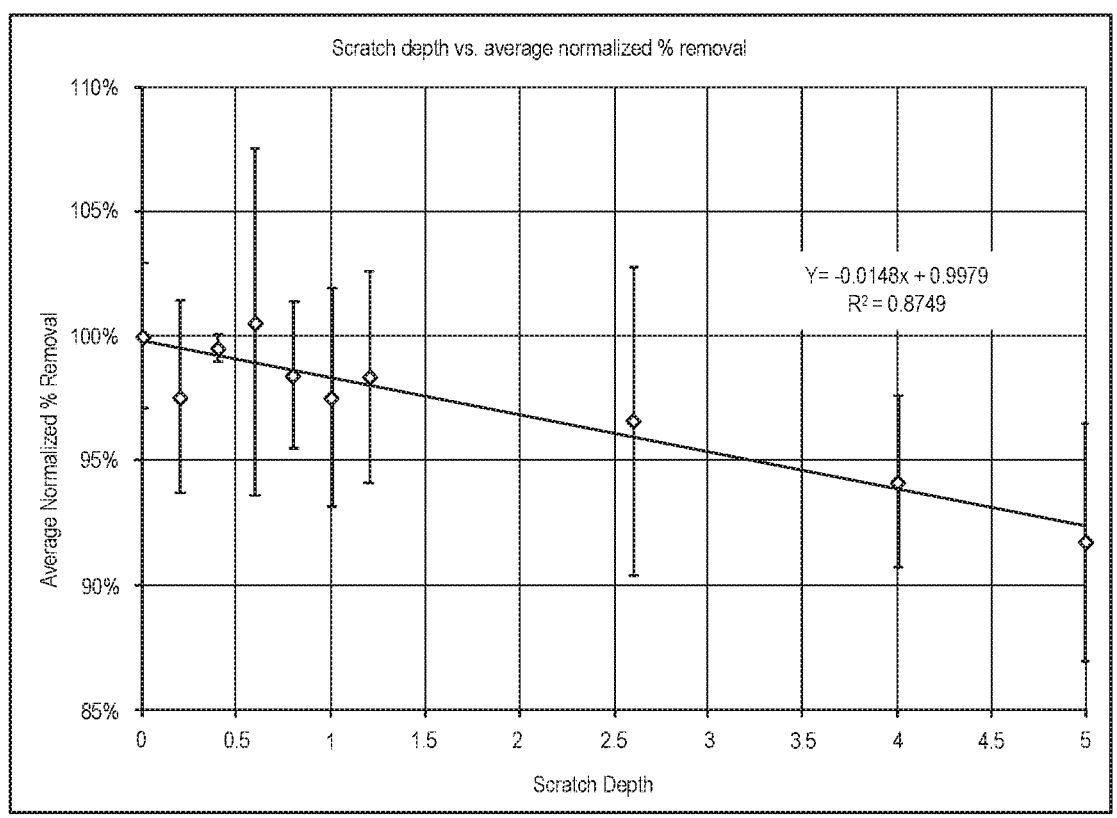
FIG. 11 illustrates linear regression of scratch depth v. average normalized % removal.

FIG. 11 illustrates linear regression of scratch depth v. average normalized % removal. Scratch depths investigated in Example 4 were determined to be significant (p-value=0.000) when analyzed using linear regression shown in FIG. 11. The regression shows that approximately 87% of the data variability could be attributed to the model, lending credibility to the findings that percent removal decreases as depth increases.

Figure 12:
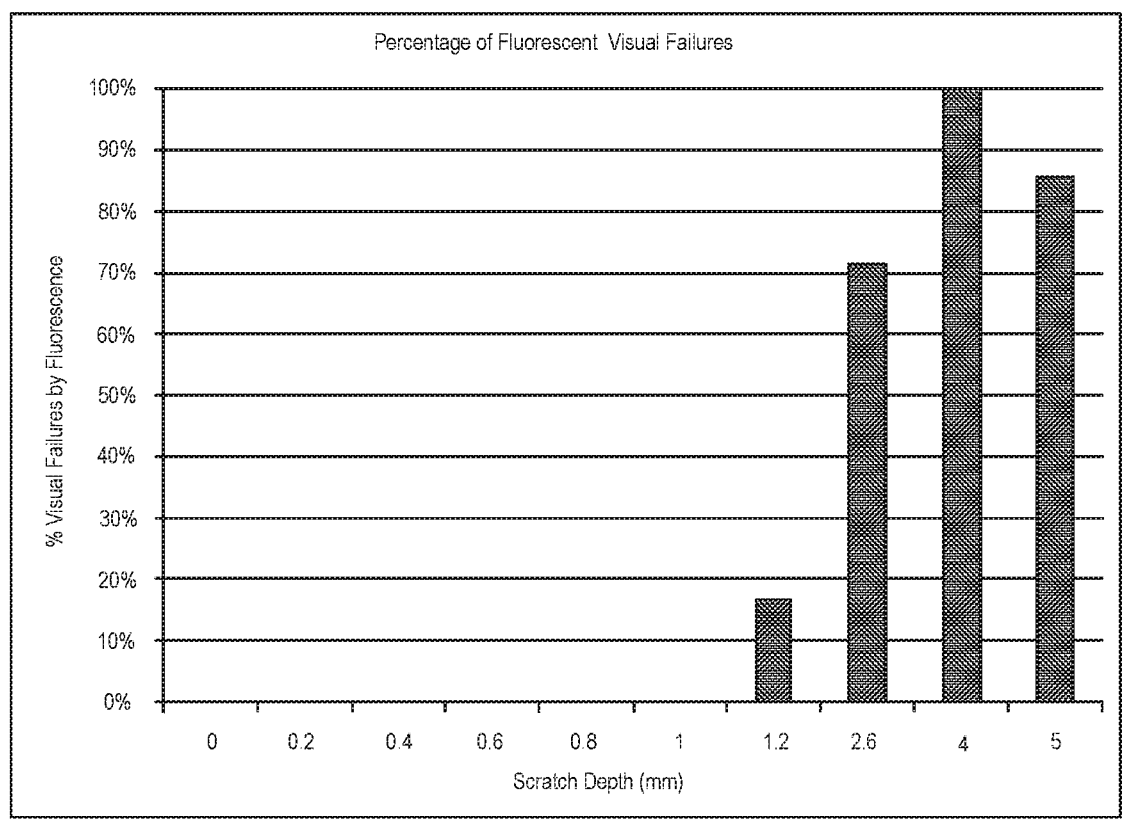
FIG. 12 illustrates the percentage of fluorescent visual failures per scratch depth.

FIG. 12 illustrates the percentage of fluorescent visual failures for Example 4. The fluorescence analysis also indicated a strong correlation on the increase in depth preventing removal of residue. As FIG. 12 shows, as the depth increased past 1.0 mm, the amount of failures during fluorescence inspection also increased. The results show the presence of scratches greater than 1.0 mm in depth can trap an amount of residue that can be observed with UV inspection of the Fluorescein.

Considering all results, a specification of ≤1.0 mm for scratches can be used as the basis for remediation as scratches greater than this depth showed visual failures within the range tested in this study.

Addendum Examples

The Addendum Examples using process soil and tank ring surrogate with various cleaning agents has a complicated interpretation where cleaning agent interaction with the soil may be the overriding factor in the results. The normalized gravimetric results are shown in Table 12. Florescent results are shown in Table 13 and TOC swab results are shown in Table 14. Where applicable, the corresponding BSA test results are shown for the same coupons.

TABLE 12

Results of % Removal for the Addendum Studies

| | Lysate | | | | Tank Ring | BSA |
|---|---|---|---|---|---|---|
| | 1% CIP100 | 1.3% CIP150 | 0.2M NaOH | Pure Water | 5% CIP100 + 5% Add | CIP 100 |
| P-04 | 87.0 ± 11.7 | 101.0 ± 7.2 | 98.2 ± 8.0 | 96.8 ± 39.2 | 90.6 ± 9.9 | 97.8 ± 2.8 |
| P-05 | 63.7 ± 28.9 | 102.6 ± 0.7 | 100.3 ± 5.4 | 98.0 ± 25.6 | 77.4 ± 32.6 | 94.1 ± 2.1 |
| P-16 | 84.7 ± 15.3 | 92.1 ± 3.3 | 96.7 ± 8.9 | 95.2 ± 21.2 | 85.9 ± 19.8 | 95.3 ± 2.6 |
| P-22 | 93.4 ± 11.2 | 100.4 ± 8.1 | 97.4 ± 7.6 | 96.4 ± 30.9 | 96.4 ± 3.9 | 98.0 ± 1.6 |
| P-23 | 68.9 ± 36.1 | 108.2 ± 3.1 | 97.9 ± 2.2 | 101.2 ± 11.3 | 74.9 ± 17.1 | 89.2 ± 1.3 |

TABLE 12-continued

Results of % Removal for the Addendum Studies

| | Lysate | | | | Tank Ring | BSA |
|---|---|---|---|---|---|---|
| | 1% CIP100 | 1.3% CIP150 | 0.2M NaOH | Pure Water | 5% CIP100 + 5% Add | CIP 100 |
| S-01 | 89.7 ± 12.0 | 101.1 ± 6.8 | 98.1 ± 5.8 | 95.3 ± 32.7 | 98.3 ± 14.0 | 97.1 ± 3.3 |
| S-04 | 81.2 ± 29.5 | 104.0 ± 5.9 | 99.2 ± 7.0 | 91.0 ± 28.0 | 87.3 ± 9.9 | 92.3 ± 3.5 |

TABLE 13

Results of Fluorescent Failures for Addendum Studies

| | Lysate | | | | BSA |
|---|---|---|---|---|---|
| | 1% CIP100 | 1.3% CIP150 | 0.2M NaOH | Pure Water | CIP 100 |
| P-04 | 0% | 0% | 0% | 0% | 0% |
| P-05 | 66% | 33% | 100% | 66% | 33% |
| P-16 | 33% | 33% | 0% | 33% | 0% |
| P-22 | 0% | 0% | 0% | 0% | 0% |
| P-23 | 66% | 100% | 100% | 66% | 66% |
| S-01 | 0% | 0% | 0% | 33% | 0% |
| S-04 | 100% | 66% | 66% | 66% | 100% |

TABLE 14

Results of TOC Analysis in Addendum Studies

| | Lysate (results in ppb carbon) | | | |
|---|---|---|---|---|
| | 1% CIP100 | 1.3% CIP150 | 0.2M NaOH | Pure Water |
| P-04 | 88.5 ± 39.1 | 220 ± 294 | 225 ± 110 | 1524 ± 169 |
| P-05 | 90.5 ± 42.4 | 217 ± 298 | 247 ± 88.2 | 1968 ± 649 |
| P-16 | 138 ± 31.5 | 171 ± 174 | 225 ± 53.3 | 1751 ± 394 |
| P-22 | 125 ± 30.3 | 136 ± 112 | 306 ± 115 | 1678 ± 220 |
| P-23 | 159 ± 73.6 | 174 ± 182 | 429 ± 324 | 1581 ± 204 |
| S-01 | 103 ± 23.0 | 160 ± 134 | 223 ± 65.6 | 1614 ± 292 |
| S-04 | 115 ± 31.3 | 204 ± 222 | 195 ± 54.1 | 1701 ± 160 |
| Control | 77.5 ± 14.9 | 175 ± 254 | 258 ± 140 | 1594 ± 336 |

Figure 13:
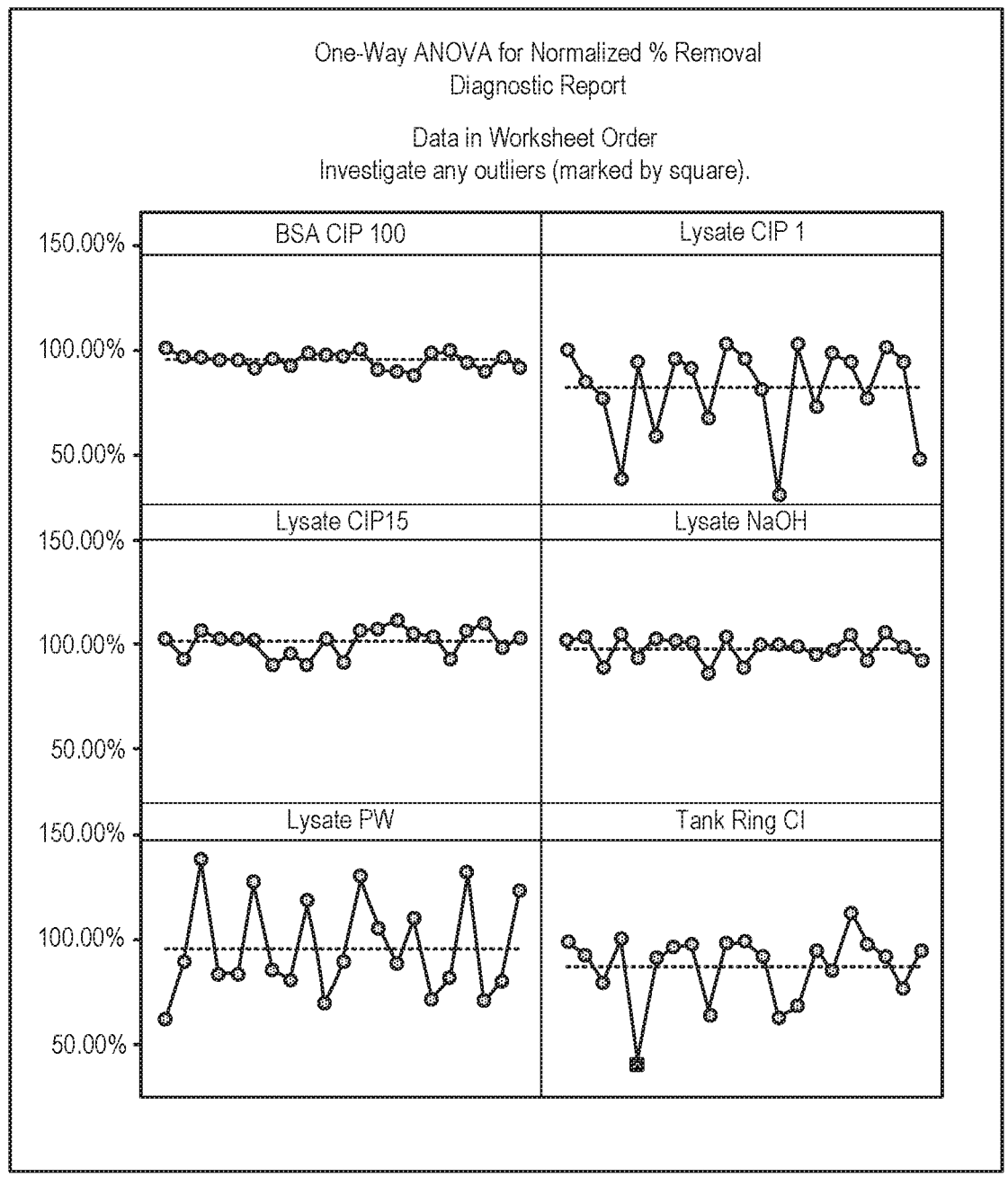
FIG. 13 illustrates ANOVA methods used in analysis of addendum studies of different challenging soils and cleaning agents.
Figure 14:
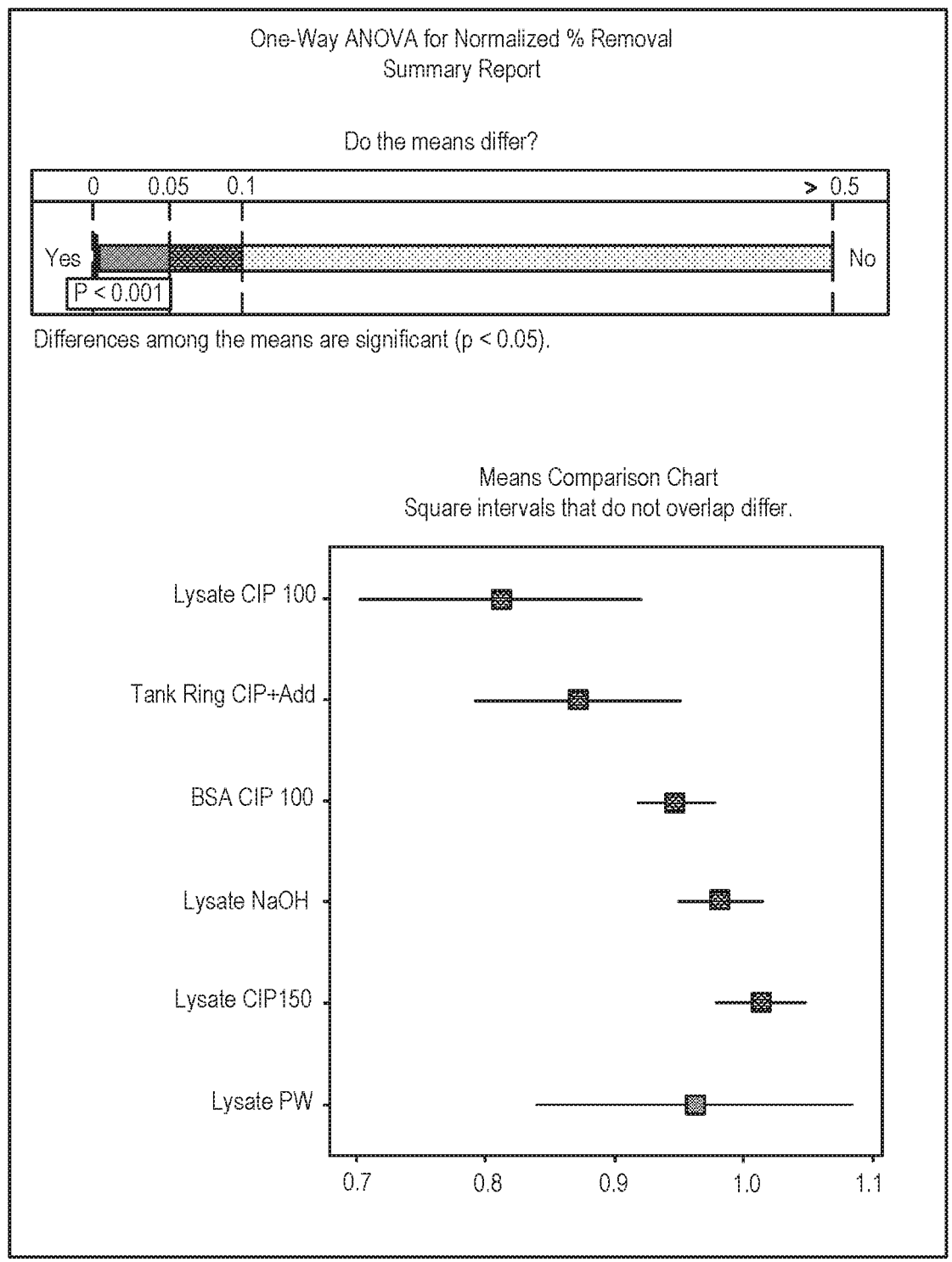
FIG. 14 illustrates ANOVA methods used in analysis of addendum studies of different challenging soils and cleaning agents.

FIGS. 13 and 14 illustrate ANOVA methods demonstrating that "Normalized % Removal" of each soil combination was a function of cleaning agent. As shown in FIGS. 13 and 14, cleaning agent affects percentage removal (p-value=0.001). As such, subsequent regression analysis was performed using the cleaning agent/soil combination as a categorical variable, as is shown in FIG. 15.

Figure 15:
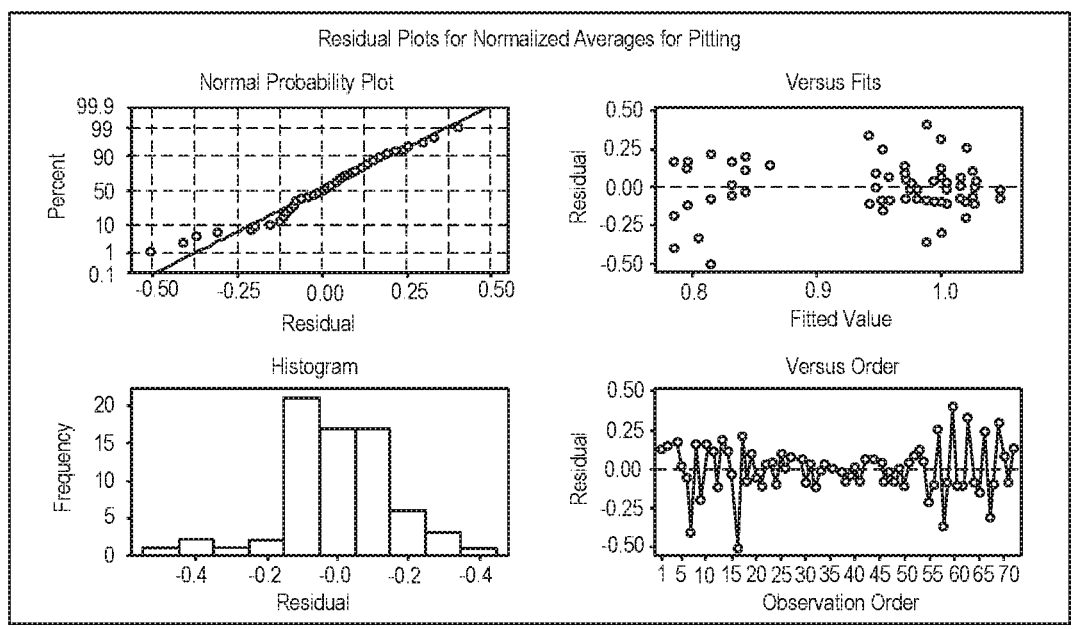
FIG. 15 illustrates multiple regression analysis for % removal as a function of density factor, aspect ratio, and depth.

FIG. 15 illustrates multiple regression analysis for % removal as a function of density factor, aspect ratio, and depth. This analysis shows that only cleaning agent is a significant factor in removal (p-value=0.007). The dominant influence of the soil/cleaning agent combination masks any underlying trends in pit behavior explored in the examples.

Figure 16:
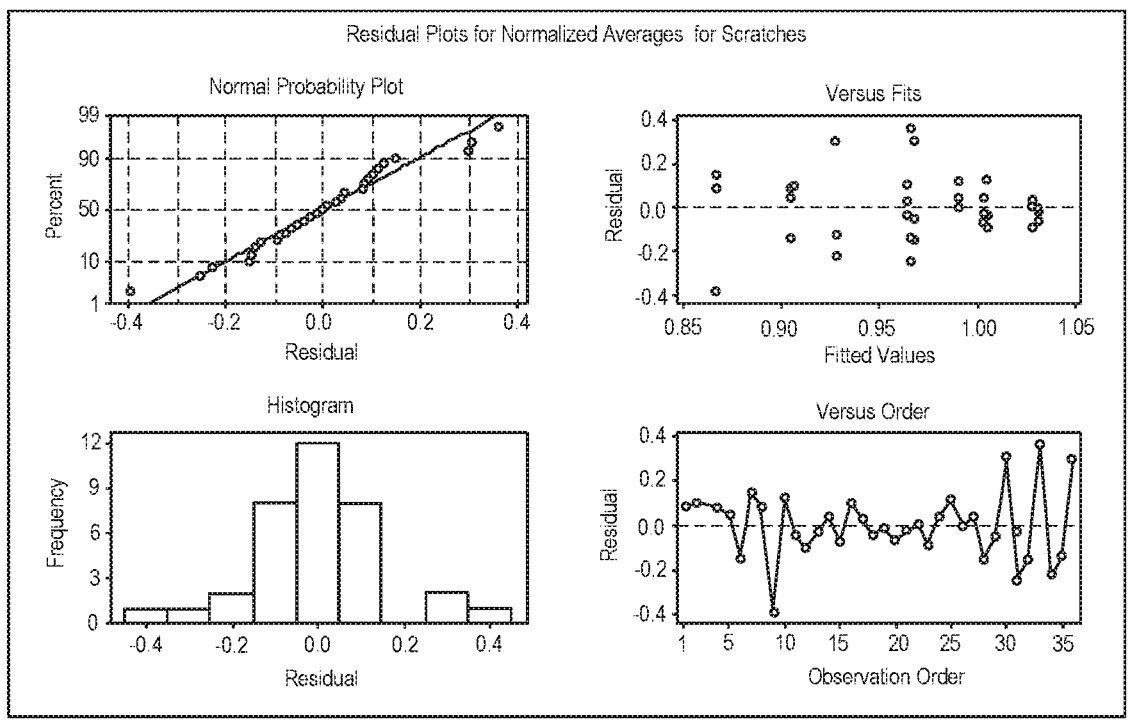
FIG. 16 illustrates multiple regression for % removal as a function of scratch depth.

FIG. 16 illustrates multiple regression for % removal as a function of scratch depth. Here, neither scratch depth nor cleaning agent was deemed to be a significant variable in the prediction of mass removal (p-value >0.05). The variability in soil removal seemed to be associated with other uncontrolled parameters, as indicated by the random distribution of removal values seen in FIG. 13.

In these Addendum Examples, a lysate soil was chosen to represent a worst-case process soil. Most of the cleaning regimens tested weren't necessarily targeted at that worst-case soil. This resulted in variability in the data where the selection of soil vs cleaning regimen is incompatible (ex. Lysate vs 1% CIP100 or purified water). In an operating facility, cleaning regimens can be chosen to target the worst-case soil within a given piece of equipment, so the variability found in the data for incompatible conditions may not necessarily reflect at-scale performance.

While no significant variables other than cleaning agent could be derived from the regression analyses, fluorescent results in Table 13 show similar trends to the behavior of the BSA surrogate. Higher depth/diameter coupons (P-05 and P-23 at 5 mm×5 mm followed by P-16 at 4 mm depth×1.2 mm diameter) show a greater propensity for inspection failures. Deeper scratches (S-04 at 4 mm) also show a greater likelihood of visual failures under the UV light. Trends in fluorescent failure for each coupon are consistent across soils and cleaners.

Turning finally to the TOC results from the study, all cleaning agent combinations were able to remove the lysate soil to the point where the average swab result was less 500 ppb TOC. Variability in swab results was lowest for the CIP 100® cleaning agent. Purified water was ineffective at removing the lysate with all swabs returning average TOC results greater than 1 ppm. To confirm, multiple regression was used to test the hypothesis that cleanability of lysate soil is a function of aspect ratio, density, pit depth, and cleaning agent. The cleaning agent established as a categorical variable in this analysis, with the purified water results removed from analysis due to the abnormally high results.

Figure 17:
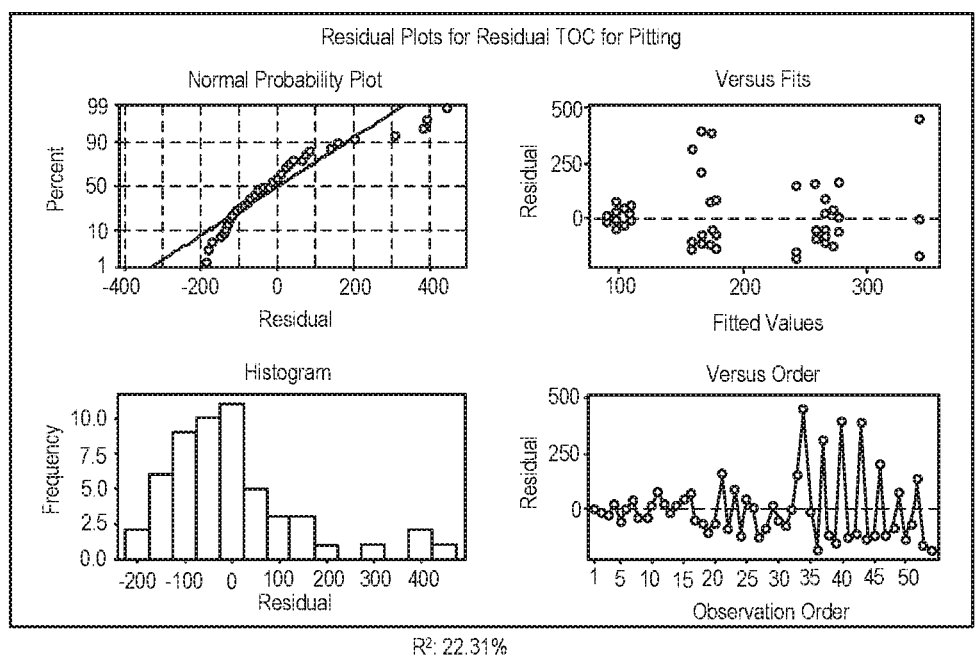
FIG. 17 illustrates multiple regression for residual TOC as a function of density factor, aspect ratio, and depth of pitting.

FIG. 17 illustrates multiple regression for % removal as a function of density factor, aspect ratio, and depth of pitting. The regression results from the TOC assessment of the pitted coupons mirror those from the gravimetric assessment. This analysis shows that only cleaning agent is a significant factor in removal (p-value=0.006). The dominant influence of the soil/cleaning agent combination masks any underlying trends in pit behavior, at least within the ranges tested.

Figure 18:
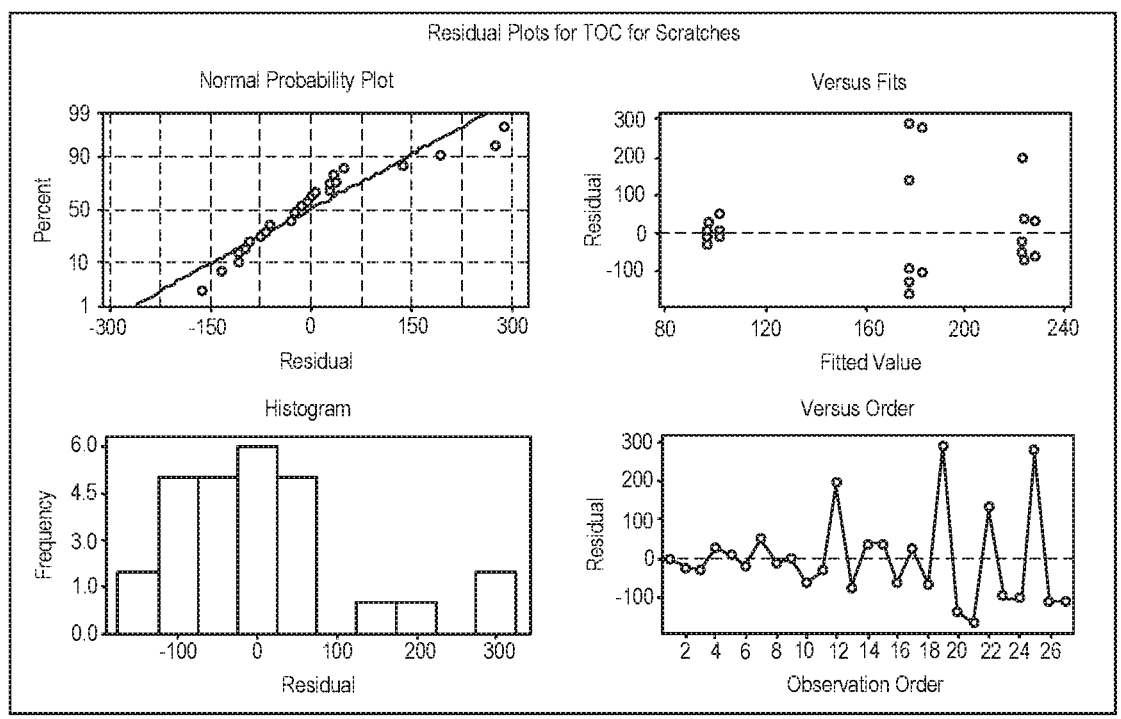
FIG. 18 illustrates residual plots for residual TOC as a function of scratch depth.

Regression results for the scratched coupons are shown in FIG. 18. That is, FIG. 18 illustrates multiple regression for % removal as a function of scratch depth. Again, neither scratch depth nor cleaning agent was deemed to be a significant variable in the prediction of mass removal (p-value >0.05). The p-value for cleaning agent was 0.097, indicating a marginal correlation between cleaning agent and TOC removal for scratched coupons than was seen in the gravimetric assessment.

Figure 19:
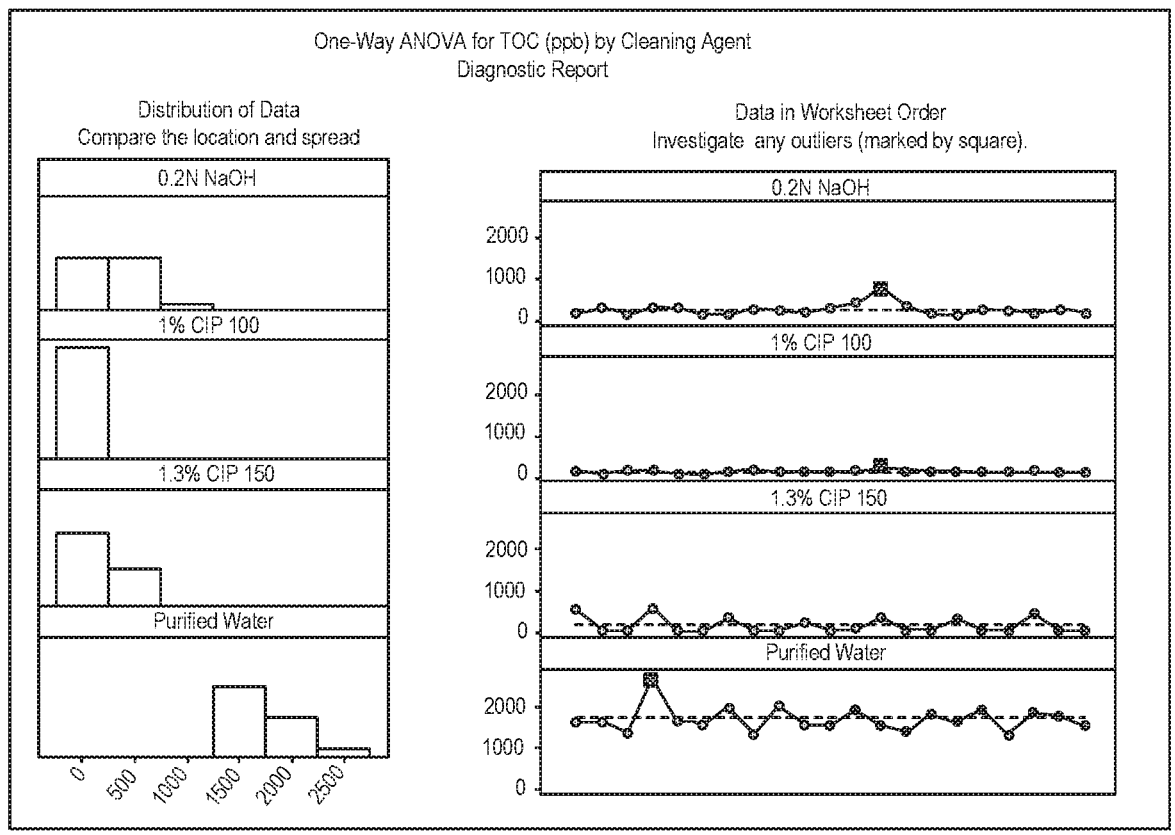
FIG. 19 illustrates a graphical summary of addendum TOC results.
Figure 20:
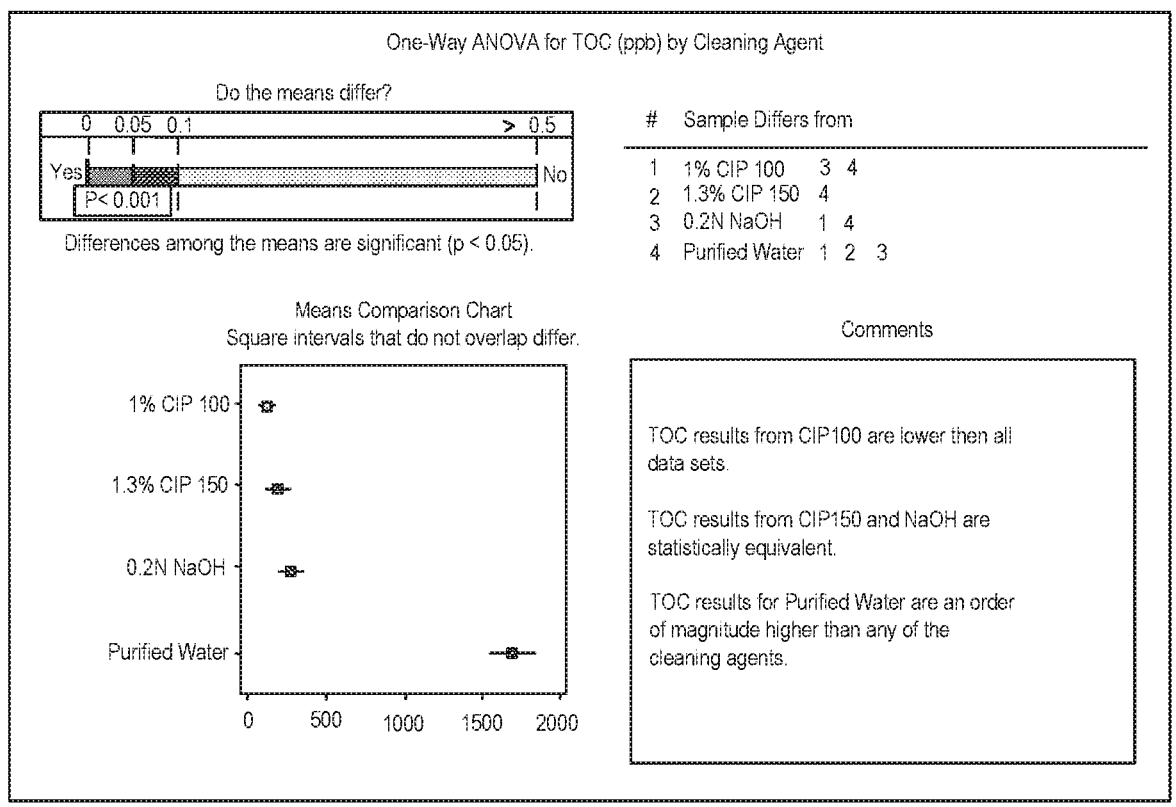
FIG. 20 illustrates ANOVA summary of addendum TOC results.

The combined TOC results for pitted and scratched coupons are compared using ANOVA in FIG. 19 and FIG. 20. FIG. 19 illustrates a graphical summary of addendum TOC results. FIG. 20 illustrates ANOVA summary of addendum TOC results. The ANOVA shows that aggregate TOC results were statistically lower with CIP-100 than any other cleaning agent (p-value <0.05). Results for CIP-150 and NaOH were indistinguishable (p-value >0.05) with the purified water results showing TOC values one order of magnitude higher than any cleaning agent. This analysis supports the claim that the addendum study results were dominated by the cleaning agent interaction with the soil.

Discussion of Examples

The results of Examples 1-4 and the Addendum Examples indicate that surface anomalies lesser than the inflection points are unlikely to impact cleanability of equipment at scale using standard CIP cleaning techniques and chemicals.

Pits: Statistical analysis of the pit data with the BSA surrogate revealed no significant correlations between aspect ratio, depth, and density (p-value >0.05). However, both pit depth (p-value=0.091) and the interaction between pit depth and aspect ratio (p-value=0.064) were near the threshold for statistical significance and may indicate marginal influence. This indicates that the depth to diameter interaction may be important for residue removal, which was supported by contour plots derived from the regression model data and presented in FIG. 7. These graphical results indicate that the quadrant with diameter ≥3.5 mm and depth ≥2.5 mm are likely to have a negative impact on cleaning efficiency.

Further observation of fluorescent material within the pits and material on the surface suggested specific inflection points beyond which coupons were not cleaned as well as unblemished surfaces. Specifically, material was consistently found in pits with diameter ≥4.0 mm and depth ≥2.6 mm. This trend was also seen in the regression analysis of the gravimetric data with diameter ≥2.5 mm and depth ≥3.5 mm impacting the cleaning on more of a continuous scale. As such, in some embodiments, reactor surfaces should be free of pits having a depth of greater than about 2.6 mm, and in some embodiments greater than about 1.2 mm. This result is consistent with the regression model showing a propensity for lower mass removal with higher depth and diameter combinations.

Using lysate process soil, no correlation was found between any of the pit characteristics and gravimetric or TOC removal (p-value >0.05). However, in both cases, the cleaning agents were found to be significant predictors in the mass removal (p-value=0.007) and TOC removal (p-value=0.006).

Considering all results, reactor surfaces can be maintained with a maximum pit depth of about 2.6 mm as depths greater than this value showed visual failures within the range tested in this study. In some embodiments, about 1.2 mm is the basis for remediation. Basing the specification exclusively on depth provides the fastest and most accurate field measurement. Since data show that depth only becomes important as the diameter exceeds a certain threshold, adopting pitting inspection criteria on this single variable provides a conservative approach to remediation.

Scratches: Like pits, scratches can affect cleanability with visible failures under fluorescence occurring when greater than about 1.0 mm deep. Scratches retain more of the tracking dye as the depth increased as well as a statistically significant decreased percentage removal by gravimetric measures. Statistical analysis of the scratch data with the BSA surrogate revealed a strong correlation between scratch depth and removal efficiency (p-value=0.000) with removal being degraded as scratch depth was increased. Visual inspection using the fluorescent marker detected failures when depth was greater than about 1.0 mm. Using the lysate process soil, the correlation between scratch depth and removal efficiency was not significant for both gravimetric and TOC results (p-value >0.05). However, based on the pit results, it is likely that the cleaning agent condition/soil interaction masked the relative importance of pit depth (p-value ≥0.097 for both gravimetric and TOC results).

Considering all results, reactor surfaces can be commissioned or maintained with a maximum scratch depth of about 1.0 mm.

Statistical analysis of the micropitting data revealed no statistical correlation between density factor and residual mass (p-value >0.05), at least within the ranges tested here. In addition, no fluorescent failures were noted during visual inspection. Statistical analysis of the surface roughness data revealed no statistical correlation between Ra Max (μin) value and residual mass (p-value >0.05). In addition, no fluorescent failures were noted during visual inspection.

The Addendum Examples were designed to demonstrate the utility of these parameters using in-process soils. The studies suggested that soil and cleaning agent combinations had a greater influence on removal than the surface imperfections themselves. Regardless, consistent fluorescent failure rates at high diameter and depth combinations supported by a similar trend in the gravimetric contour plot shows that similar trends in removal are seen under actual process conditions.

Table 15 summarizes the statistical conclusions from the studies with regard to gravimetric analysis of pits, scratches, and surface roughness. P-values <0.05 indicate that specific variables were deemed to be statistically significant, while the $R^2$ value indicates the percentage of the data variability that can be attributed to the regression model.

TABLE 15

Gravimetric Conclusions from BSA Testing

| Surface Imperfection Type | Regression Statistics |
|---|---|
| Micropits | $R^2$: 0.09% |
| | p-values |
| | Density Factor: 0.917 |
| Scratches | $R^2$: 87.49% |
| | p-values |
| | Depth: 0.000 |
| Surface Roughness | $R^2$: 10.30% |
| | p-values |
| | Ra: 0.135 |
| Pits | $R^2$: 33.54% |
| | p-values |
| | Density Factor: 0.706 |
| | Pit Depth: 0.091 |
| | Aspect Ratio: 0.649 |
| | Density Factor * Pit Depth: 0.455 |
| | Density Factor * Aspect Ratio: 0.500 |
| | Pit Depth * Aspect Ratio: 0.064 |

Table 16 summarizes the conclusions from the Addendum Examples with regard to gravimetric analysis. In all cases, the worst-case lysate process soil was applied to the test coupons, and residual mass was evaluated as a function of the different pit and scratch parameters. Regression was performed with cleaning agent test condition included as a categorical variable.

TABLE 16

Gravimetric Conclusions from Addendum Examples

| Surface Imperfection Type | Regression Statistics |
|---|---|
| Scratches | $R^2$: 9.91% |
| | p-values |
| | Depth: 0.504 |
| | Cleaning Agent: 0.443 |

TABLE 16-continued

Gravimetric Conclusions from Addendum Examples

| Surface Imperfection Type | Regression Statistics |
|---|---|
| Pits | $R^2$: 19.83%<br>p-values<br>Density Factor: 0.881<br>Pit Depth: 0.618<br>Aspect Ratio: 0.694<br>Density Factor * Pit Depth: 0.857<br>Pit Depth * Aspect Ratio: 0.697<br>Cleaning Agent: 0.007 |

Table 17 summarizes the conclusions from the addendum Examples with regard to residual TOC detected from swab sampling. In all cases, the resulting TOC value represents the amount of lysate soil that could be detected after cleaning. Regression was again performed on the data to assess the impact of pits and scratches on residual TOC. The cleaning agent test conditions were included as a categorical variable. Results exclude values obtained after rinse with purified water at 80° C. as all TOC swabs exceeded 1 ppm under these conditions:

TABLE 17

TOC Conclusions from Addendum Study

| Surface Imperfection Type | Regression Statistics |
|---|---|
| Scratches | $R^2$: 18.37%<br>p-values<br>Depth: 0.922<br>Cleaning Agent: 0.097 |
| Pits | $R^2$: 22.31%<br>p-values<br>Density Factor: 0.911<br>Pit Depth: 0.930<br>Aspect Ratio: 0.960<br>Density Factor * Pit Depth: 0.561<br>Pit Depth * Aspect Ratio: 0.950<br>Cleaning Agent: 0.006 |

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The descriptions of the various embodiments of the present invention can be utilized in the production of pharmaceuticals and biopharmaceutical products. The devices, facilities and methods described herein are suitable for culturing any desired cell line including prokaryotic and/or eukaryotic cell lines. Further, in embodiments, the devices, facilities and methods are suitable for culturing suspension cells or anchorage-dependent (adherent) cells and are suitable for production operations configured for production of pharmaceutical and biopharmaceutical products—such as polypeptide products, nucleic acid products (for example DNA or RNA), or cells and/or viruses such as those used in cellular and/or viral therapies.

In embodiments, the cells express or produce a product, such as a recombinant therapeutic or diagnostic product. As described in more detail below, examples of products produced by cells include, but are not limited to, antibody molecules (e.g., monoclonal antibodies, bispecific antibodies), antibody mimetics (polypeptide molecules that bind specifically to antigens but that are not structurally related to antibodies such as e.g. DARPins, affibodies, adnectins, or IgNARs), fusion proteins (e.g., Fc fusion proteins, chimeric cytokines), other recombinant proteins (e.g., glycosylated proteins, enzymes, hormones), viral therapeutics (e.g., anti-cancer oncolytic viruses, viral vectors for gene therapy and viral immunotherapy), cell therapeutics (e.g., pluripotent stem cells, mesenchymal stem cells and adult stem cells), vaccines or lipid-encapsulated particles (e.g., exosomes, virus-like particles), RNA (such as e.g. siRNA) or DNA (such as e.g. plasmid DNA), antibiotics or amino acids. In embodiments, the devices, facilities and methods can be used for producing biosimilars.

As mentioned, in embodiments, devices, facilities and methods allow for the production of eukaryotic cells, e.g., mammalian cells or lower eukaryotic cells such as for example yeast cells or filamentous fungi cells, or prokaryotic cells such as Gram-positive or Gram-negative cells and/or products of the eukaryotic or prokaryotic cells, e.g., proteins, peptides, antibiotics, amino acids, nucleic acids (such as DNA or RNA), synthesised by the eukaryotic cells in a large-scale manner. Unless stated otherwise herein, the devices, facilities, and methods can include any desired volume or production capacity including but not limited to bench-scale, pilot-scale, and full production scale capacities.

Moreover and unless stated otherwise herein, the devices, facilities, and methods can include any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermentor or fermentation unit, or any other reaction vessel and the term "reactor" is used interchangeably with "fermentor." For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and CO2 levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316L or any other suitable stainless steel) and Inconel, plastics, and/or glass.

In embodiments and unless stated otherwise herein, the devices, facilities, and methods described herein can also include any suitable unit operation and/or equipment not otherwise mentioned, such as operations and/or equipment for separation, purification, and isolation of such products. Any suitable facility and environment can be used, such as traditional stick-built facilities, modular, mobile and temporary facilities, or any other suitable construction, facility, and/or layout. For example, in some embodiments modular clean-rooms can be used. Additionally and unless otherwise stated, the devices, systems, and methods described herein can be housed and/or performed in a single location or facility or alternatively be housed and/or performed at separate or multiple locations and/or facilities.

By way of non-limiting examples and without limitation, U.S. Publication Nos. 2013/0280797; 2012/0077429; 2011/0280797; 2009/0305626; and U.S. Pat. Nos. 8,298,054; 7,629,167; and 5,656,491, which are hereby incorporated by reference in their entirety, describe example facilities, equipment, and/or systems that may be suitable.

In embodiments, the cells are eukaryotic cells, e.g., mammalian cells. The mammalian cells can be for example human or rodent or bovine cell lines or cell strains. Examples of such cells, cell lines or cell strains are e.g. mouse myeloma (NSO)-cell lines, Chinese hamster ovary (CHO)-cell lines, HT1080, H9, HepG2, MCF7, MDBK Jurkat, NIH3T3, PC12, BHK (baby hamster kidney cell), VERO, SP2/0, YB2/0, Y0, C127, L cell, COS, e.g., COS1 and COST, QC1-3, HEK-293, VERO, PER.C6, HeLA, EB1, EB2, EB3, oncolytic or hybridoma-cell lines. Preferably the mammalian cells are CHO-cell lines. In one embodiment, the cell is a CHO cell. In one embodiment, the cell is a CHO-K1 cell, a CHO-K1 SV cell, a DG44 CHO cell, a DUXB11 CHO cell, a CHOS, a CHO GS knock-out cell, a CHO FUT8 GS knock-out cell, a CHOZN, or a CHO-derived cell. The CHO GS knock-out cell (e.g., GSKO cell) is, for example, a CHO-K1 SV GS knockout cell. The CHO FUT8 knockout cell is, for example, the Potelligent® CHOK1 SV (Lonza Biologics, Inc.). Eukaryotic cells can also be avian cells, cell lines or cell strains, such as for example, EBx® cells, EB14, EB24, EB26, EB66, or EBv13.

In one embodiment, the eukaryotic cells are stem cells. The stem cells can be, for example, pluripotent stem cells, including embryonic stem cells (ESCs), adult stem cells, induced pluripotent stem cells (iPSCs), tissue specific stem cells (e.g., hematopoietic stem cells) and mesenchymal stem cells (MSCs).

In one embodiment, the cell is a differentiated form of any of the cells described herein. In one embodiment, the cell is a cell derived from any primary cell in culture.

In embodiments, the cell is a hepatocyte such as a human hepatocyte, animal hepatocyte, or a non-parenchymal cell. For example, the cell can be a plateable metabolism qualified human hepatocyte, a plateable induction qualified human hepatocyte, plateable Qualyst Transporter Certified™ human hepatocyte, suspension qualified human hepatocyte (including 10-donor and 20-donor pooled hepatocytes), human hepatic kupffer cells, human hepatic stellate cells, dog hepatocytes (including single and pooled Beagle hepatocytes), mouse hepatocytes (including CD-1 and C57Bl/6 hepatocytes), rat hepatocytes (including Sprague-Dawley, Wistar Han, and Wistar hepatocytes), monkey hepatocytes (including Cynomolgus or Rhesus monkey hepatocytes), cat hepatocytes (including Domestic Shorthair hepatocytes), and rabbit hepatocytes (including New Zealand White hepatocytes). Example hepatocytes are commercially available from Triangle Research Labs, LLC, 6 Davis Drive Research Triangle Park, N.C., USA 27709.

In one embodiment, the eukaryotic cell is a lower eukaryotic cell such as e.g. a yeast cell (e.g., *Pichia* genus (e.g. *Pichia pastoris*, *Pichia methanolica*, *Pichia kluyveri*, and *Pichia angusta*), *Komagataella* genus (e.g. *Komagataella pastoris*, *Komagataella pseudopastoris* or *Komagataella phaffii*), *Saccharomyces* genus (e.g. *Saccharomyces cerevisae*, *cerevisiae*, *Saccharomyces kluyveri*, *Saccharomyces uvarum*), *Kluyveromyces* genus (e.g. *Kluyveromyces lactis*, *Kluyveromyces marxianus*), the *Candida* genus (e.g. *Candida utilis*, *Candida cacaoi*, *Candida boidinii*), the *Geotrichum* genus (e.g. *Geotrichum fermentans*), *Hansenula polymorpha*, *Yarrowia lipolytica*, or *Schizosaccharomyces pombe*. Preferred is the species *Pichia pastoris*. Examples for *Pichia pastoris* strains are X33, GS115, KM71, KM71H; and CBS7435.

In one embodiment, the eukaryotic cell is a fungal cell (e.g. *Aspergillus* (such as *A. niger*, *A. fumigatus*, *A. orzyae*, *A. nidula*), *Acremonium* (such as *A. thermophilum*), *Chaetomium* (such as *C. thermophilum*), *Chrysosporium* (such as *C. thermophile*), *Cordyceps* (such as *C. militaris*), *Corynascus*, *Ctenomyces*, *Fusarium* (such as *F. oxysporum*), *Glomerella* (such as *G. graminicola*), *Hypocrea* (such as *H. jecorina*), *Magnaporthe* (such as *M. orzyae*), *Myceliophthora* (such as *M. thermophile*), *Nectria* (such as *N. heamatococca*), *Neurospora* (such as *N. crassa*), *Penicillium*, *Sporotrichum* (such as *S. thermophile*), *Thielavia* (such as *T. terrestris*, *T. heterothallica*), *Trichoderma* (such as *T. reesei*), or *Verticillium* (such as *V. dahlia*)).

In one embodiment, the eukaryotic cell is an insect cell (e.g., Sf9, Mimic™ Sf9, Sf21, High Five™ (BT1-TN-5B1-4), or BT1-Ea88 cells), an algae cell (e.g., of the genus *Amphora*, *Bacillariophyceae*, *Dunaliella*, *Chlorella*, *Chlamydomonas*, *Cyanophyta* (cyanobacteria), *Nannochloropsis*, *Spirulina*, or *Ochromonas*), or a plant cell (e.g., cells from monocotyledonous plants (e.g., maize, rice, wheat, or *Setaria*), or from a dicotyledonous plants (e.g., cassava, potato, soybean, tomato, tobacco, alfalfa, *Physcomitrella patens* or *Arabidopsis*).

In one embodiment, the cell is a bacterial or prokaryotic cell.

In embodiments, the prokaryotic cell is a Gram-positive cells such as *Bacillus*, *Streptomyces Streptococcus*, *Staphylococcus* or *Lactobacillus*. *Bacillus* that can be used is, e.g. the *B. subtilis*, *B. amyloliquefaciens*, *B. licheniformis*, *B. natto*, or *B. megaterium*. In embodiments, the cell is *B. subtilis*, such as *B. subtilis* 3NA and *B. subtilis* 168. *Bacillus* is obtainable from, e.g., the *Bacillus* Genetic Stock Center, Biological Sciences 556, 484 West 12$^{th}$ Avenue, Columbus Ohio 43210-1214.

In one embodiment, the prokaryotic cell is a Gram-negative cell, such as *Salmonella* spp. or *Escherichia coli*, such as e.g., TG1, TG2, W3110, DH1, DHB4, DH5a, HMS 174, HMS174 (DE3), NM533, C600, HB101, JM109, MC4100, XL1-Blue and Origami, as well as those derived from *E. coli* B-strains, such as for example BL-21 or BL21 (DE3), all of which are commercially available.

Suitable host cells are commercially available, for example, from culture collections such as the DSMZ (Deutsche Sammlung von Mikroorganismen and Zellkulturen GmbH, Braunschweig, Germany) or the American Type Culture Collection (ATCC).

In embodiments, the cultured cells are used to produce proteins e.g., antibodies, e.g., monoclonal antibodies, and/or recombinant proteins, for therapeutic use. In embodiments, the cultured cells produce peptides, amino acids, fatty acids or other useful biochemical intermediates or metabolites. For example, in embodiments, molecules having a molecular weight of about 4000 daltons to greater than about 140,000 daltons can be produced. In embodiments, these molecules can have a range of complexity and can include posttranslational modifications including glycosylation.

In embodiments, the protein is, e.g., BOTOX, Myobloc, Neurobloc, Dysport (or other serotypes of botulinum neurotoxins), alglucosidase alpha, daptomycin, YH-16, choriogonadotropin alpha, filgrastim, cetrorelix, interleukin-2, aldesleukin, teceleulin, denileukin diftitox, interferon alpha-n3 (injection), interferon alpha-n1, DL-8234, interferon, Suntory (gamma-1a), interferon gamma, thymosin alpha 1, tasonermin, DigiFab, ViperaTAb, EchiTAb, CroFab, nesiritide, abatacept, alefacept, Rebif, eptoterminalfa, teriparatide (osteoporosis), calcitonin injectable (bone disease), calcitonin (nasal, osteoporosis), etanercept, hemoglobin glutamer 250 (bovine), drotrecogin alpha, collagenase, carperitide, recombinant human epidermal growth factor (topical gel, wound healing), DWP401, darbepoetin alpha, epoetin omega, epoetin beta, epoetin alpha, desirudin, lepirudin, bivalirudin, nonacog alpha, Mononine, eptacog alpha (activated), recombinant Factor VIII+VWF, Recombinate, recombinant Factor VIII, Factor VIII (recombinant), Alphnmate, octocog alpha, Factor VIII, palifermin, Indikinase, tenecteplase, alteplase, pamiteplase, reteplase, nateplase, monteplase, follitropin alpha, rFSH, hpFSH, micafungin, pegfilgrastim, lenograstim, nartograstim, sermorelin, glucagon, exenatide, pramlintide, iniglucerase, galsulfase, Leucotropin, molgramostim, triptorelin acetate, histrelin (subcutaneous implant, Hydron), deslorelin, histrelin, nafarelin, leuprolide sustained release depot (ATRIGEL), leuprolide implant (DUROS), goserelin, Eutropin, KP-102 program, somatropin, mecasermin (growth failure), enlfavirtide, Org-33408, insulin glargine, insulin glulisine, insulin (inhaled), insulin lispro, insulin detemir, insulin (buccal, RapidMist), mecasermin rinfabate, anakinra, celmoleukin, 99 mTc-apcitide injection, myelopid, Betaseron, glatiramer acetate, Gepon, sargramostim, oprelvekin, human leukocyte-derived alpha interferons, Bilive, insulin (recombinant), recombinant human insulin, insulin aspart, mecasenin, Roferon-A, interferon-alpha 2, Alfaferone, interferon alfacon-1, interferon alpha, Avonex' recombinant human luteinizing hormone, dornase alpha, trafermin, ziconotide, taltirelin, diboterminalfa, atosiban, becaplermin, eptifibatide, Zemaira, CTC-111, Shanvac-B, HPV vaccine (quadrivalent), octreotide, lanreotide, ancestirn, agalsidase beta, agalsidase alpha, laronidase, prezatide copper acetate (topical gel), rasburicase, ranibizumab, Actimmune, PEG-Intron, Tricomin, recombinant house dust mite allergy desensitization injection, recombinant human parathyroid hormone (PTH) 1-84 (sc, osteoporosis), epoetin delta, transgenic antithrombin III, Granditropin, Vitrase, recombinant insulin, interferon-alpha (oral lozenge), GEM-21S, vapreotide, idursulfase, omnapatrilat, recombinant serum albumin, certolizumab pegol, glucarpidase, human recombinant C1 esterase inhibitor (angioedema), lanoteplase, recombinant human growth hormone, enfuvirtide (needle-free injection, Biojector 2000), VGV-1, interferon (alpha), lucinactant, aviptadil (inhaled, pulmonary disease), icatibant, ecallantide, omiganan, Aurograb, pexigananacetate, ADI-PEG-20, LDI-200, degarelix, cintredelinbesudotox, Favld, MDX-1379, ISAtx-247, liraglutide, teriparatide (osteoporosis), tifacogin, AA4500, T4N5 liposome lotion, catumaxomab, DWP413, ART-123, Chrysalin, desmoteplase, amediplase, corifollitropinalpha, TH-9507, teduglutide, Diamyd, DWP-412, growth hormone (sustained release injection), recombinant G-CSF, insulin (inhaled, AIR), insulin (inhaled, Technosphere), insulin (inhaled, AERx), RGN-303, DiaPep277, interferon beta (hepatitis C viral infection (HCV)), interferon alpha-n3 (oral), belatacept, transdermal insulin patches, AMG-531, MBP-8298, Xerecept, opebacan, AIDS-VAX, GV-1001, LymphoScan, ranpirnase, Lipoxysan, lusupultide, MP52 (beta-tricalciumphosphate carrier, bone regeneration), melanoma vaccine, sipuleucel-T, CTP-37, Insegia, vitespen, human thrombin (frozen, surgical bleeding), thrombin, TransMID, alfimeprase, Puricase, terlipressin (intravenous, hepatorenal syndrome), EUR-1008M, recombinant FGF-I (injectable, vascular disease), BDM-E, rotigaptide, ETC-216, P-113, MBI-594AN, duramycin (inhaled, cystic fibrosis), SCV-07, OPI-45, Endostatin, Angiostatin, ABT-510, Bowman Birk Inhibitor Concentrate, XMP-629, 99 mTc-Hynic-Annexin V, kahalalide F, CTCE-9908, teverelix (extended release), ozarelix, rornidepsin, BAY-504798, interleukin4, PRX-321, Pepscan, iboctadekin, rhlactoferrin, TRU-015, IL-21, ATN-161, cilengitide, Albuferon, Biphasix, IRX-2, omega interferon, PCK-3145, CAP-232, pasireotide, huN901-DMI, ovarian cancer immunotherapeutic vaccine, SB-249553, Oncovax-CL, OncoVax-P, BLP-25, CerVax-16, multi-epitope peptide melanoma vaccine (MART-1, gp100, tyrosinase), nemifitide, rAAT (inhaled), rAAT (dermatological), CGRP (inhaled, asthma), pegsunercept, thymosinbeta4, plitidepsin, GTP-200, ramoplanin, GRASPA, OBI-1, AC-100, salmon calcitonin (oral, eligen), calcitonin (oral, osteoporosis), examorelin, capromorelin, Cardeva, velafermin, 1311-TM-601, KK-220, T-10, ularitide, depelestat, hematide, Chrysalin (topical), rNAPc2, recombinant Factor V111 (PEGylated liposomal), bFGF, PEGylated recombinant staphylokinase variant, V-10153, SonoLysis Prolyse, NeuroVax, CZEN-002, islet cell neogenesis therapy, rGLP-1, BIM-51077, LY-548806, exenatide (controlled release, Medisorb), AVE-0010, GA-GCB, avorelin, ACM-9604, linaclotid eacetate, CETi-1, Hemospan, VAL (injectable), fast-acting insulin (injectable, Viadel), intranasal insulin, insulin (inhaled), insulin (oral, eligen), recombinant methionyl human leptin, pitrakinra subcutancous injection, eczema), pitrakinra (inhaled dry powder, asthma), Multikine, RG-1068, MM-093, NBI-6024, AT-001, PI-0824, Org-39141, Cpn10 (autoimmune diseases/ inflammation), talactoferrin (topical), rEV-131 (ophthalmic), rEV-131 (respiratory disease), oral recombinant human insulin (diabetes), RPI-78M, oprelvekin (oral), CYT-99007 CTLA4-Ig, DTY-001, valategrast, interferon alpha-n3 (topical), IRX-3, RDP-58, Tauferon, bile salt stimulated lipase, Merispase, alaline phosphatase, EP-2104R, Melanotan-II, bremelanotide, ATL-104, recombinant human microplasmin, AX-200, SEMAX, ACV-1, Xen-2174, CJC-1008, dynorphin A, SI-6603, LAB GHRH, AER-002, BGC-728, malaria vaccine (virosomes, PeviPRO), ALTU-135, parvovirus B19 vaccine, influenza vaccine (recombinant neuraminidase), malaria/HBV vaccine, anthrax vaccine, Vacc-5q, Vacc-4x, HIV vaccine (oral), HPV vaccine, Tat Toxoid, YSPSL, CHS-13340, PTH(1-34) liposomal cream (Novasome), Ostabolin-C, PTH analog (topical, psoriasis), MBRI-93.02, MTB72F vaccine (tuberculosis), MVA-Ag85A vaccine (tuberculosis), FARA04, BA-210, recombinant plague FIV vaccine, AG-702, OxSODrol, rBetV1, Der-p1/Der-p2/Der-p7 allergen-targeting vaccine (dust mite allergy), PR1 peptide antigen (leukemia), mutant ras vaccine, HPV-16 E7 lipopeptide vaccine, labyrinthin vaccine (adenocarcinoma), CML vaccine, WT1-peptide vaccine (cancer), IDD-5, CDX-110, Pentrys, Norelin, CytoFab, P-9808, VT-111, icrocaptide, telbermin (dermatological, diabetic foot ulcer), rupintrivir, reticulose, rGRF, HA, alpha-galactosidase A, ACE-011, ALTU-140, CGX-1160, angiotensin therapeutic vaccine, D-4F, ETC-642, APP-018, rhMBL, SCV-07 (oral, tuberculosis), DRF-7295, ABT-828, ErbB2-specific immunotoxin (anticancer), DT3SSIL-3, TST-10088, PRO-1762, Combotox, cholecystokinin-B/gastrin-receptor binding peptides, 111In-hEGF, AE-37, trasnizumab-DM1, Antagonist G, IL-12 (recombinant), PM-02734, IMP-321, rhIGF-BP3, BLX-883, CUV-1647 (topical), L-19 based radioimmunotherapeutics (cancer), Re-188-P-2045, AMG-386, DC/1540/KLH vaccine (cancer), VX-001, AVE-9633, AC-9301, NY-ESO-1 vaccine (peptides), NA17.A2 peptides, melanoma vaccine (pulsed antigen therapeutic), prostate cancer vaccine, CBP-501, recombinant human lactoferrin (dry eye), FX-06, AP-214, WAP-8294A (injectable), ACP-HIP, SUN-11031, peptide YY [3-36] (obesity, intranasal), FGLL, atacicept, BR3-Fc, BN-003, BA-058, human parathyroid hormone 1-34 (nasal, osteoporosis), F-18-CCR1, AT-1100 (celiac disease/diabetes), JPD-003, PTH(7-34) liposomal cream (Novasome), duramycin (ophthalmic, dry eye), CAB-2, CTCE-0214, GlycoPEGylated erythropoietin, EPO-Fc, CNTO-528, AMG-114, JR-013, Factor XIII, aminocandin, PN-951, 716155, SUN-E7001, TH-0318, BAY-73-7977, teverelix (immediate release), EP-51216, hGH (controlled release, Biosphere), OGP-I, sifuvirtide, TV4710, ALG-889, Org-41259, rhCC10, F-991, thymopentin (pulmonary diseases), r(m)CRP, hepatoselective insulin, subalin, L19-IL-2 fusion protein, elafin, NMK-150, ALTU-139, EN-122004, rhTPO, thrombopoietin receptor agonist (thrombocytopenic disorders), AL-108, AL-208, nerve growth factor antagonists (pain), SLV-317, CGX-1007, INNO-105, oral teriparatide (eligen), GEM-OS1, AC-162352, PRX-302, LFn-p24 fusion vaccine (Therapore), EP-1043, *S pneumoniae* pediatric vaccine, malaria vaccine, *Neisseria meningitidis* Group B vaccine, neonatal group B streptococcal vaccine, anthrax vaccine, HCV vaccine (gpE1+gpE2+MF-59), otitis media therapy, HCV vaccine (core antigen+ISCOMATRIX), hPTH(1-34) (transdermal, ViaDerm), 768974, SYN-101, PGN-0052, aviscumnine, BIM-23190, tuberculosis vaccine, multi-epitope tyrosinase peptide, cancer vaccine, enkastim, APC-8024, GI-5005, ACC-001, TTS-CD3, vascular-targeted TNF (solid tumors), desmopressin (buccal controlled-release), onercept, and TP-9201.

In some embodiments, the polypeptide is adalimumab (HUMIRA), infliximab (REMICADE™), rituximab (RITUXAN™/MAB THERA™) etanercept (ENBREL™), bevacizumab (AVASTIN™), trastuzumab (HERCEPTIN™), pegrilgrastim (NEULASTA™), or any other suitable polypeptide including biosimilars and biobetters.

Other suitable polypeptides are those listed below and in Table 1 of US2016/0097074:

TABLE I

| Protein Product | Reference Listed Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |

TABLE I-continued

| Protein Product | Reference Listed Drug |
|---|---|
| Interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | BEXXAR ® |
| antihemophilic factor | Bioclate ™ |
| human growth hormone | BioTropin ™ |
| botulinum toxin type A | BOTOX ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune fab [ovine] | DigiFab ™ |
| Rasburicase | Elitek ® |
| Etanercept | ENBREL ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | FORTEO ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | HEMOFIL |
| adefovir dipivoxil | Hepsera ™ |
| Trastuzumab | Herceptin ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| eptifibatide | Integrilin ™ |
| alpha-interferon | Intron A ® |
| Palifermin | Kepivance |
| Anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa for injection | Luveris |
| OspA lipoprotein | LYMErix ™ |
| Ranibizumab | LUCENTIS ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolesomab | NeutroSpec ® (formerly LeuTech ®) |
| somatropin [rDNA] | Norditropin ®/Norditropin Nordiflex ® |
| Mitoxantrone | Novantrone ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |

TABLE I-continued

| Protein Product | Reference Listed Drug |
|---|---|
| PEG-L-asparaginase | Oncaspar ® |
| abatacept, fully human soluable fusion protein | Orencia ™ |
| muromomab-CD3 | Orthoclone OKT3 ® |
| high-molecular weight hyaluronan | Orthovisc ® |
| human chorionic gonadotropin | Ovidrel ® |
| live attenuated Bacillus Calmette-Guerin | Pacis ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | RAPTIVA ™ |
| combination of ribavirin and alpha interferon | Rebetron ™ |
| Interferon beta 1a | Rebif ® |
| antihemophilic factor | Recombinate ® rAHF/ |
| antihemophilic factor | ReFacto ® |
| Lepirudin | Refludan ® |
| Infliximab | REMICADE ® |
| Abciximab | ReoPro ™ |
| Reteplase | Retavase ™ |
| Rituxima | Rituxan ™ |
| interferon alfa-2$^a$ | Roferon-A ® |
| Somatropin | Saizen ® |
| synthetic porcine secretin | SecreFlo ™ |
| Basiliximab | Simulect ® |
| Eculizumab | SOLIRIS (R) |
| Pegvisomant | SOMAVERT ® |
| Palivizumab; recombinantly produced, humanized mAb | Synagis ™ |
| thyrotropin alfa | Thyrogen ® |
| Tenecteplase | TNKase ™ |
| Natalizumab | TYSABRI ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In embodiments, the polypeptide is a hormone, blood clotting/coagulation factor, cytokine/growth factor, antibody molecule, fusion protein, protein vaccine, or peptide as shown in Table 2.

TABLE 2

Exemplary Products

| Therapeutic Product type | Product | Trade Name |
|---|---|---|
| Hormone | Erythropoietin, Epoein-α | Epogen, Procrit |
| | Darbepoetin-α | Aranesp |
| | Growth hormone (GH), somatotropin | Genotropin, Humatrope, Norditropin, NovIVitropin, Nutropin, Omnitrope, Protropin, Siazen, Serostim, Valtropin |
| | Human follicle-stimulating hormone (FSH) | Gonal-F, Follistim |
| | Human chorionic gonadotropin | Ovidrel Luveris |
| | Lutropin-α | GlcaGen |
| | Glucagon | Geref |
| | Growth hormone releasing hormone (GHRH) | ChiRhoStim (human peptide), SecreFlo (porcine peptide) |
| | Secretin | |
| | Thyroid stimulating hormone (TSH), thyrotropin | Thyrogen |
| Blood Clotting/ Coagulation Factors | Factor VIIa | NovoSeven |
| | Factor VIII | Bioclate, Helixate, Kogenate, Recombinate, ReFacto |
| | Factor IX | Benefix |
| | Antithrombin III (AT-III) | Thrombate III |
| | Protein C concentrate | Ceprotin |
| Cytokine/ Growth factor | Type I alpha-interferon | Infergen |
| | Interferon-αn3 (IFNαn3) | Alferon N |
| | Interferon-β1a (rIFN-β) | Avonex, Rebif |
| | Interferon-β1b (rIFN-β) | Betaseron |
| | Interferon-γ1b (IFN γ) | Actimmune |
| | Aldesleukin (interleukin 2(IL2), epidermal theymocyte activating factor; ETAF | Proleukin Kepivance Regranex Anril, Kineret |
| | Palifermin (keratinocyte growth factor; KGF) | |
| | Becaplemin (platelet-derived growth factor; PDGF) | |
| | Anakinra (recombinant IL1 antagonist) | |
| Antibody molecules | Bevacizumab (VEGFA mAb) | Avastin |
| | Cetuximab (EGFR mAb) | Erbitux |
| | Panitumumab (EGFR mAb) | Vectibix Campath Rituxan |
| | Alemtuzumab (CD52 mAb) | Herceptin Orencia |
| | Rituximab (CD20 chimeric Ab) | Humira Enbrel |
| | Trastuzumab (HER2/Neu mAb) | Remicade Amevive |
| | Abatacept (CTLA Ab/Fc fusion) | Raptiva Tysabri |
| | Adalimumab (TNFα mAb) | Soliris Orthoclone, OKT3 |
| | Etanercept (TNF receptor/Fc fusion) | |
| | Infliximab (TNFα chimeric mAb) | |
| | Alefacept (CD2 fusion protein) | |
| | Efalizumab (CD11a mAb) | |
| | Natalizumab (integrin α4 subunit mAb) | |
| | Eculizumab (C5mAb) | |
| | Muromonab-CD3 | |
| Other: Fusion proteins/ Protein vaccines/ Peptides | Insulin | Humulin, Novolin |
| | Hepatitis B surface antigen (HBsAg) | Engerix, Recombivax HB |
| | HPV vaccine | Gardasil |
| | OspA | LYMErix |
| | Anti-Rhesus(Rh) immunoglobulin G | Rhophylac Fuzeon |
| | Enfuvirtide | QMONOS |
| | Spider silk, e.g., fibrion | |

In embodiments, the protein is multispecific protein, e.g., a bispecific antibody as shown in Table 3.

TABLE 3

| Bispecific Formats | | | | | |
|---|---|---|---|---|---|
| Name (other names, sponsoring organizations) | BsAb format | Targets | Proposed mechanisms of action | Development stages | Diseases (or healthy volunteers) |
| Catumaxomab (Removab ®, Fresenius Biotech, Trion Pharma, Neopharm) | BsIgG: Triomab | CD3, EpCAM | Retargeting of T cells to tumor, Fc mediated effector functions | Approved in EU | Malignant ascites in EpCAM positive tumors |
| Ertumaxomab (Neovii Biotech, Fresenius Biotech) | BsIgG: Triomab | CD3, HER2 | Retargeting of T cells to tumor | Phase I/II | Advanced solid tumors |
| Blinatumomab (Blincyto ®, AMG 103, MT 103, MEDI 538, Amgen) | BiTE | CD3, CD19 | Retargeting of T cells to tumor | Approved in USA Phase II and III Phase II Phase I | Precursor B-cell ALL ALL DLBCL NHL |
| REGN1979 (Regeneron) | BsAb | CD3, CD20 | | | |
| Solitomab (AMG 110, MT110, Amgen) | BiTE | CD3, EpCAM | Retargeting of T cells to tumor | Phase I | Solid tumors |
| MEDI 565 (AMG 211, MedImmune, Amgen) | BiTE | CD3, CEA | Retargeting of T cells to tumor | Phase I | Gastrointestinal adenocancinoma |
| RO6958688 (Roche) | BsAb | CD3, CEA | | | |
| BAY2010112 (AMG 212, Bayer; Amgen) | BiTE | CD3, PSMA | Retargeting of T cells to tumor | Phase I | Prostate cancer |
| MGD006 (Macrogenics) | DART | CD3, CD123 | Retargeting of T cells to tumor | Phase I | AML |
| MGD007 (Macrogenics) | DART | CD3, gpA33 | Retargeting of T cells to tumor | Phase I | Colorectal cancer |
| MGD011 (Macrogenics) | DART | CD19, CD3 | | | |
| SCORPION (Emergent Biosolutions, Trubion) | BsAb | CD3, CD19 | Retargeting of T cells to tumor | | |
| AFM11 (Affimed Therapeutics) | TandAb | CD3, CD19 | Retargeting of T cells to tumor | Phase I | NHL and ALL |
| AFM12 (Affimed Therapeutics) | TandAb | CD19, CD16 | Retargeting of NK cells to tumor cells | | |
| AFM13 (Affimed Therapeutics) | TandAb | CD30, CD16A | Retargeting of NK cells to tumor cells | Phase II | Hodgkin's Lymphoma |
| GD2 (Barbara Ann Karmanos Cancer Institute) | T cells preloaded with BsAb | CD3, GD2 | Retargeting of T cells to tumor | Phase I/II | Neuroblastoma and osteosarcoma |
| pGD2 (Barbara Ann Karmanos Cancer Institute) | T cells preloaded with BsAb | CD3, Her2 | Retargeting of T cells to tumor | Phase II | Metastatic breast cancer |
| EGFRBi-armed autologous activated T cells (Roger Williams Medical Center) | T cells preloaded with BsAb | CD3, EGFR | Autologous activated T cells to EGFR-positive tumor | Phase I | Lung and other solid tumors |
| Anti-EGFR-armed activated T-cells (Barbara Ann Karmanos Cancer Institute) | T-cells preloaded with BsAb | CD3, EGFR | Autologous activated T cells to EGFR-positive tumor | Phase I | Colon and pancreatic cancers |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| rM28 (University Hospital Tübingen) | Tandem scFv | CD28, MAPG | Retargeting of T cells to tumor | Phase II | Metastatic melanoma |
| IMCgp100 (Immunocore) | ImmTAC | CD3, peptide MHC | Retargeting of T cells to tumor | Phase I/II | Metastatic melanoma |
| DT2219ARL (NCI, University of Minnesota) | 2 scFv linked to diphtheria toxin | CD19, CD22 | Targeting of protein toxin to tumor | Phase I | B cell leukemia or lymphoma |
| XmAb5871 (Xencor) | BsAb | CD19, CD32b | | | |
| NI-1701 (NovImmune) | BsAb | CD47, CD19 | | | |
| MM-111 (Merrimack) | BsAb | ErbB2, ErbB3 | | | |
| MM-141 (Merrimack) | BsAb | IGF-1R, ErbB3 | | | |
| NA (Merus) | BsAb | HER2, HER3 | | | |
| NA (Merus) | BsAb | CD3, CLEC12A | | | |
| NA (Merus) | BsAb | EGFR, HER3 | | | |
| NA (Merus) | BsAb | PD1, undisclosed | | | |
| NA (Merus) | BsAb | CD3, undisclosed | | | |
| Duligotuzumab (MEHD7945A, Genentech, Roche) | DAF | EGFR, HER3 | Blockade of 2 receptors, ADCC | Phase I and II Phase II | Head and neck cancer Colorectal cancer |
| LY3164530 (Eli Lily) | Not disclosed | EGFR, MET | Blockade of 2 receptors | Phase I | Advanced or metastatic cancer |
| MM-111 (Merrimack Pharmaceuticals) | HSA body | HER2, HER3 | Blockade of 2 receptors | Phase II Phase I | Gastric and esophageal cancers Breast cancer |
| MM-141, (Merrimack Pharmaceuticals) | IgG-scFv | IGF-1R, HER3 | Blockade of 2 receptors | Phase I | Advanced solid tumors |
| RG7221 (RO5520985, Roche) | CrossMab | Ang2, VEGF A | Blockade of 2 proangiogenics | Phase I | Solid tumors |
| RG7716 (Roche) | CrossMab | Ang2, VEGF A | Blockade of 2 proangiogenics | Phase I | Wet AMD |
| OMP-305B83 (OncoMed) | BsAb | DLL4/VEGF | | | |
| TF2 (Immunomedics) | Dock and lock | CEA, HSG | Pretargeting tumor for PET or radioimaging | Phase II | Colorectal, breast and lung cancers |
| ABT-981 (AbbVie) | DVD-Ig | IL-1α, IL-1β | Blockade of 2 proinflammatory cytokines | Phase II | Osteoarthritis |
| ABT-122 (AbbVie) | DVD-Ig | TNF, IL-17A | Blockade of 2 proinflammatory cytokines | Phase II | Rheumatoid arthritis |
| COVA322 | IgG-fynomer | TNF, IL17A | Blockade of 2 proinflammatory cytokines | Phase I/II | Plaque psoriasis |
| SAR156597 (Sanofi) | Tetravalent bispecific tandem IgG | IL-13, IL-4 | Blockade of 2 proinflammatory cytokines | Phase I | Idiopathic pulmonary fibrosis |
| GSK2434735 (GSK) | Dual-targeting domain | IL-13, IL-4 | Blockade of 2 proinflammatory cytokines | Phase I | (Healthy volunteers) |

TABLE 3-continued

Bispecific Formats

| Name (other names, sponsoring organizations) | BsAb format | Targets | Proposed mechanisms of action | Development stages | Diseases (or healthy volunteers) |
|---|---|---|---|---|---|
| Ozoralizumab (ATN103, Ablynx) | Nanobody | TNF, HSA | Blockade of proinflammatory cytokine, binds to HSA to increase half-life | Phase II | Rheumatoid arthritis |
| ALX-0761 (Merck Serono, Ablynx) | Nanobody | IL-17A/F, HSA | Blockade of 2 proinflammatory cytokines, binds to HSA to increase half-life | Phase I | (Healthy volunteers) |
| ALX-0061 (AbbVie, Ablynx; | Nanobody | IL-6R, HSA | Blockade of proinflammatory cytokine, binds to HSA to increase half-life | Phase I/II | Rheumatoid arthritis |
| ALX-0141 (Ablynx, Eddingpharm) | Nanobody | RANKL, HSA | Blockade of bone resorption, binds to HSA to increase half-life | Phase I | Postmenopausal bone loss |
| RG6013/ACE910 (Chugai, Roche) | ART-Ig | Factor IXa, factor X | Plasma coagulation | Phase II | Hemophilia |

What is claimed is:

1. A biopharmaceutical processing equipment, comprising:
a vessel defining a volume for receiving a proteinaceous processing material, the vessel having an interior reactor surface that is configured to contact proteinaceous processing material when contained within the volume of the vessel, the biopharmaceutical processing equipment further comprising a clean-in-place (CIP) apparatus configured to clean the surface, and wherein the interior reactor surface is made from stainless steel and has a pre-commissioning surface roughness of greater than or equal to about 25 Ra Max (μin) and less than or equal to about 250 Ra Max (μin);
a nutrient inlet for feeding a nutrient to a proteinaceous processing material contained in the vessel volume;
an outlet for removing a proteinaceous processing material from the vessel;
a pH sensor for monitoring a pH level in the vessel; and
a gas sensor for monitoring a dissolved gas in a proteinaceous processing material contained in the vessel volume.

2. The biopharmaceutical processing equipment of claim 1, wherein the surface has a pre-commissioning surface roughness of greater than about 35 Ra Max (μin) and less than or equal to about 250 Ra Max (μin).

3. The biopharmaceutical processing equipment of claim 1, wherein the surface has a pre-commissioning surface roughness of greater than about 90 Ra Max (μin) and less than or equal to about 150 Ra Max (μin).

4. The biopharmaceutical processing equipment of claim 1, wherein the surface has a pre-commissioning surface roughness of about 150 Ra Max (μin).

5. The biopharmaceutical processing equipment of claim 1, wherein the surface is formed of 316L stainless steel.

6. The biopharmaceutical processing equipment of claim 1, wherein the gas sensor is configured to monitor dissolved oxygen or dissolved carbon dioxide.

7. A biopharmaceutical processing equipment, comprising:
a vessel defining a volume for receiving a proteinaceous processing material, the vessel having an interior reactor surface that is configured to contact proteinaceous processing material when contained within the volume of the vessel, and wherein the interior reactor surface is made from stainless steel and has a thickness of greater than 2.6 mm, and wherein the surface has a surface finish that is free of a surface anomaly that exceeds a maximum depth of surface pitting of about 2.6 mm;
a nutrient inlet for feeding a nutrient to a proteinaceous processing material contained in the vessel volume;
an outlet for removing a proteinaceous processing material from the vessel;
a pH sensor for monitoring a pH level in the vessel; and
a gas sensor for monitoring a dissolved gas in a proteinaceous processing material contained in the vessel volume.

8. The biopharmaceutical processing equipment of claim 7, wherein the processing equipment surface is free of a surface anomaly that exceeds a maximum scratch depth of about 1.0 mm.

9. The biopharmaceutical processing equipment of claim 7, wherein the surface is free of a surface anomaly that exceeds a maximum depth of surface pitting of about 1.2 mm.

10. The biopharmaceutical processing equipment of claim 7, wherein the surface is formed of 316L stainless steel.

11. The biopharmaceutical processing equipment of claim 7, wherein the surface has a pre-commissioning surface roughness of greater than about 20 Ra Max (μin).

12. The biopharmaceutical processing equipment of claim 7, wherein the surface has a pre-commissioning surface roughness of greater than about 35 Ra and less than or equal to about 250 Ra Max (μin).

13. The biopharmaceutical processing equipment of claim 7, wherein the surface has a pre-commissioning surface roughness of about 150 Ra Max (μin).

14. The biopharmaceutical processing equipment of claim 7, wherein the surface has a surface finish that is free of a surface anomaly that exceeds any of: a maximum depth of surface pitting of about 1.2 mm, and a maximum scratch depth of about 1.0 mm.

15. The biopharmaceutical processing equipment of claim 7, wherein the gas sensor is configured to monitor dissolved oxygen or dissolved carbon dioxide.

16. A biopharmaceutical processing equipment, comprising:
   a vessel defining a volume for receiving a proteinaceous processing material, the vessel having an interior reactor surface that is configured to contact proteinaceous processing material when contained within the volume of the vessel, and wherein the interior reactor surface is made from stainless steel and has a pre-commissioning surface roughness of greater than or equal to about 40 Ra Max (μin) and less than or equal to about 250 Ra Max (μin);
   a nutrient inlet for feeding a nutrient to a proteinaceous processing material contained in the vessel volume;
   an outlet for removing a proteinaceous processing material from the vessel;
   a pH sensor for monitoring a pH level in the vessel; and
   a gas sensor for monitoring a dissolved gas in a proteinaceous processing material contained in the vessel volume.

17. The biopharmaceutical processing equipment of claim 16, wherein the gas sensor is configured to monitor dissolved oxygen or dissolved carbon dioxide.

* * * * *